(12) United States Patent
Heyes et al.

(10) Patent No.: US 7,745,651 B2
(45) Date of Patent: Jun. 29, 2010

(54) CATIONIC LIPIDS AND METHODS OF USE

(75) Inventors: James Heyes, Vancouver (CA); Ian MacLachlan, Vancouver (CA); Lorne R. Palmer, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 604 days.

(21) Appl. No.: 11/148,430

(22) Filed: Jun. 7, 2005

(65) Prior Publication Data

US 2006/0083780 A1 Apr. 20, 2006

Related U.S. Application Data

(60) Provisional application No. 60/679,427, filed on May 9, 2005, provisional application No. 60/610,746, filed on Sep. 17, 2004, provisional application No. 60/578,075, filed on Jun. 7, 2004.

(51) Int. Cl.
  *C07C 229/00* (2006.01)
  *C07B 35/00* (2006.01)
  *C07B 37/00* (2006.01)
  *A01N 31/70* (2006.01)
  *A01N 43/04* (2006.01)
  *A61K 31/70* (2006.01)
  *A61K 9/48* (2006.01)
  *A61B 8/00* (2006.01)

(52) U.S. Cl. .................. 554/103; 424/9.51; 424/450; 554/105; 554/108; 554/110; 554/127; 514/44

(58) Field of Classification Search .............. None
See application file for complete search history.

(56) References Cited

U.S. PATENT DOCUMENTS

| | | | |
|---|---|---|---|
| 4,394,448 A | 7/1983 | Szoka, Jr. et al. | |
| 4,438,052 A | 3/1984 | Weder et al. | |
| 4,515,736 A | 5/1985 | Deamer | |
| 4,598,051 A | 7/1986 | Papahadjopoulos et al. | |
| 4,897,355 A | 1/1990 | Eppstein et al. | |
| 5,013,556 A | 5/1991 | Woodle et al. | |
| 5,171,678 A | 12/1992 | Behr et al. | |
| 5,208,036 A | 5/1993 | Eppstein et al. | |
| 5,225,212 A | 7/1993 | Martin et al. | |
| 5,264,618 A | 11/1993 | Felgner et al. | |
| 5,279,833 A | 1/1994 | Rose | |
| 5,283,185 A | 2/1994 | Epand et al. | |
| 5,320,906 A | 6/1994 | Eley et al. | |
| 5,545,412 A | 8/1996 | Eppstein et al. | |
| 5,578,475 A | 11/1996 | Jessee et al. | |
| 5,641,662 A | 6/1997 | Debs et al. | |
| 5,656,743 A | 8/1997 | Busch et al. | |
| 5,703,055 A | 12/1997 | Felgner et al. | |
| 5,705,385 A | 1/1998 | Bally et al. | |
| 5,820,873 A | 10/1998 | Choi et al. | |
| 5,976,567 A | 11/1999 | Wheeler et al. | |
| 5,981,501 A | 11/1999 | Wheeler et al. | |
| 6,534,484 B1 | 3/2003 | Wheeler et al. | |
| 6,586,410 B1 | 7/2003 | Wheeler et al. | |
| 6,649,780 B1 * | 11/2003 | Eibl et al. .................. 554/110 |
| 6,815,432 B2 | 11/2004 | Wheeler et al. | |
| 6,858,224 B2 | 2/2005 | Wheeler et al. | |
| 2003/0077829 A1 | 4/2003 | MacLachlan | |
| 2003/0125263 A1 | 7/2003 | Gold et al. | |
| 2003/0143732 A1 | 7/2003 | Fosnaugh et al. | |
| 2004/0063654 A1 | 4/2004 | Davis et al. | |
| 2004/0142892 A1 | 7/2004 | Finn et al. | |
| 2004/0253723 A1 | 12/2004 | Tachas et al. | |
| 2004/0259247 A1 | 12/2004 | Tuschl et al. | |
| 2006/0105976 A1 | 5/2006 | Soutschek et al. | |

FOREIGN PATENT DOCUMENTS

| | | |
|---|---|---|
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 01/05374 A1 | 1/2001 |
| WO | WO 02/34236 A2 | 5/2002 |
| WO | WO 02/087541 A1 | 11/2002 |
| WO | WO 03/097805 A2 | 11/2003 |
| WO | WO 2004/065546 A2 | 8/2004 |
| WO | WO 2004/110499 A1 | 12/2004 |
| WO | WO 2005/007196 A2 | 1/2005 |
| WO | WO 2005/026372 A1 | 3/2005 |
| WO | WO 2005/120152 A2 | 12/2005 |

OTHER PUBLICATIONS

Arpicco et al., 1999, Proceed. Int'l Symp. Control. Rel. Bioact. Mater. 26:7759-760 (+face page).*

(Continued)

*Primary Examiner*—Robert M Kelly
*Assistant Examiner*—Kelaginamane Hiriyanna
(74) *Attorney, Agent, or Firm*—Townsend and Townsend and Crew LLP

(57) ABSTRACT

The present invention provides compositions comprising cationic lipids, liposomes and nucleic acid-lipid particles comprising the cationic lipids, and methods of using such compositions, liposomes, and nucleic acid-lipid particles.

4 Claims, 15 Drawing Sheets

OTHER PUBLICATIONS

Ballas, N. et al., "Liposomes bearing a quartemary ammonium detergent as an efficient vehicle for functional transfer of TMV-RNA into plant protoplasts," *Biochim. Biophys. Acta*, 1998, pp. 8-18, vol. 939.

Barinaga, M., "Step Taken Toward Improved Vectors for Gene Transfer," *Science*, 1994, p. 1326, vol. 266.

Behr, J-P., "Synthetic Gene-Transfer Vectors," *Acc. Chem. Res.* 1993, pp. 274-278, vol. 26.

Brigham, K. et al., "Rapid Communication: In vivo Transfection of Murine Lungs with a Functioning Prokaryotic Gene Using a Liposome Vehicle," *Am. J. Med. Sci.*, 1989, pp. 278-281, vol. 298.

Cortesi, R., et al.. "Effect of cationic liposome composition on in vitro cytotoxicity and protective effect on carried DNA," *International Journal of Pharmaceutics*, 1996, pp. 69-78, vol. 139.

Crystal, R., "Transfer of Genes to Humans: Early Lessons and Obstacles to Success," *Science*, 1995, pp. 404-410, vol. 270.

Culver K.,, "The First Human Gene Therapy Experiment," *Gene Therapy: A Handbook for Physicians*, 1994, pp. 33-40.

Duzgunes, N., "Membrane Fusion," *Subcellular Biochemistry*, 1985, pp. 195-286, vol. 11.

Dwarki, V.J., et al., "Cationic Liposime-Mediated RNA Transfection." *Methods in Enzymology*, 1993, pp. 644-654, vol. 217.

Enoch, H. et al., "Formation and properties of 1000-Å-diameter, single-bilayer phospholipid vesicles," *Proc. Natl. Acad. Sci. USA*, 1979, pp. 145-149, vol. 76, No. 1.

Felgner, P. et al., "Lipofection: A highly efficient, lipid-mediated DNA-transfection procedure," *Proc. Natl. Acad. Sci. USA*, 1987, pp. 7413-7417, vol. 84.

Felgner, J.H., et al., "Enhanced Gene Delivery and Mechanism Studies with a Novel Series of Cationic Lipid Formulations," *The Journal of Biological Chemistry*, Jan. 1994, pp. 2550-2561, vol. 269, No. 4.

Felgner, J., et al., "Cationic Lipid-Mediated Transfection in Mammalian Cells: "Lipofection"," *J. Tiss. Cult. Meth.*, 1993, pp. 63-68, vol. 15.

Felgner, P.L., et al., "Cationic Liposome Mediated Transfection," *Proc. West. Pharmacol. Soc.*, 1989, pp. 115-121, vol. 32.

Gao, X. et al., "A Novel Cationic Liposome Reagent for Efficient Transfection of Mammalian Cells," *Biochem. Biophys. Res. Comm.*, 1991, pp. 280-285, vol. 179.

Gershon, H. et al., "Mode of Formation and Structural Feature of DNA-Cationic Liposome Complexes Used for Transfection," *Biochemistry*, 1993, pp. 7413-7151, vol. 32.

Guy-Caffey, J., et al., "Novel Polyaminolipids Enhance the Cellular Uptake of Oligonucleotides," *The Journal of Biological Chemistry*, Dec. 1995, pp. 31391-31396, vol. 270, No. 52.

Hawley-Nelson, et al., "LipofectAmine™ Reagent: A New, Higher Efficiency Polycationic Liposome Transfection Reagent," *Focus*, 1993, p. 73-80, vol. 15, No. 3.

Hyde, S., et al., "Correction of the ion transport defect in cystic fibrosis transgenic mice by gene therapy," *Nature*, 1993, pp. 250-256, vol. 362.

Jiang, Lei et al.; "Comparison of protein precipitation methods for sample preparation prior to proteomic analysis"; 2004, *Journal of Chromatography*, vol. 1023, No. 2, pp. 317-320.

Juliano R., and Stamp, D., "The Effect of Particle Size and Charge on the Clearance Rates of Liposomes and Liposome Encapsulated Drugs," *Biochem. Biophys. Res. Commun.*, 1975, pp. 651-658, vol. 63.

Legendre, J.Y. and Szoka, F., "Delivery of Plasmid DNA into Mammalian Cell Lines Using pH-Sensitive Liposomes: Comparison with Cationic Liposomes," *Pharm. Res.*, 1992, pp. 1235-1242, vol. 9, No. 10.

Leventis, R., et al.,, "Interactions of mammalian cells with lipid dispersions containing novel metabolizable cationic amphiphiles," *Biochem. Blophys. Acta*, 1990, p. 124, vol. 1023.

Marshall, E., "Gene Therapy's Growing Pains," *Science*, 1995, pp. 1050-1055. vol. 269.

Orkin, et al., *NIH Report, Report and Recommendations of the Panel to Assess the NIH Investment in Research on Gene Therapy*, 1995.

Paul, Cynthia P. et al.; "Effective expression of small Interfering RNA in human cells"; 2002, *Nature Biotechnology*, vol. 20, pp. 505-508.

Puyal, C., et al., "A new cationic liposome encapsulating genetic material: A potential delivery system for polynucleotides," *Eur. J. Biochem.*, 1995, pp. 697-703, vol. 228.

Spagnou, Sebastien et al.; "Lipidic Carriers of siRNA: Differences in the Formulation, Cellular Uptake, and Delivery with Plasmid DNA"; 2004, *Biochemistry*, vol. 43, pp. 13348-13356.

Stamatatos, L., et al., "Interactions of Cationic Lipid Vesicles with Negatively Charged Phospholipid Vesicles and Biological Membranes," *Biochemistry*, 1988, pp. 3917-3925, vol. 27.

Szoka, F. et al., "Comparative Properties and Methods of Preparation of Lipid Vesicles (Liposomes)," *Ann. Rev. Biophys. Bioeng.*, 1980, pp. 467-508, vol. 9.

Szoka, F. et al., "Procedure for preparation of liposomes with large internal aqueous space and high capture by reverse-phase evaporation," *Proc. Natl. Acad. Sci. USA*, 1978, pp. 4194-4198, vol. 75, No. 9.

Van Der Woude, I., et al., "Parameters influencing the Introduction of plasmid DNA into cells by the use of synthetic amphiphiles as a carrier system," *Biochimica et Biophysica Acta*, 1995, pp. 34-40, vol. 1240.

Wilson, R. et al., "Counterion-Induced Condensation of Deoxyribonucleic Acid. A Light-Scattering Study." *Biochemistry*, 1979, pp. 2192-2196, vol. 18.

Woodle, M.C. et al., "Versatility in lipid compositions showing prolonged circulation with sterically stabilized liposomes," *Biochem. Biophys. Acta*, 1992, pp. 193-200, vol. 1105.

Zhu, N., et al., "Systemic Gene Expression After Intravenous DNA Delivery into Adult Mice," *Science*, 1993, pp. 209-211, vol. 261.

PCT—International Search Report.

S. Arpicco et al., Preparation and Characterization of Novel Cationic Lipids Developed for Gene Transfection, Dipartimento di Scienza e Tecnologia del Farmaco, Via P. Giuria 9, 10125 Torino, Italy.

S. Arpicco et al., Synthesis, characterization and transfection activity of new saturated and unsaturated cationic lipids, Science Direct, 2004, 869-878, IL Farmaco 59.

Heyes, James et al. "Cationic lipid saturation influences intracellular delivery of encapsulated nucleic acids," Journal of Controlled Release, 2005, vol. 107, pp. 276-287.

Heyes, James et al. "Synthesis of Novel Cationic Lipids: Effect of Structural Modification on the Efficiency of Gene Transfer," J. Med. Chem., 2002, vol. 45, pp. 99-114.

Arpicco S. et al., "Synthesis, Characterization and Transfection Activity of New Saturated and Unsaturated Cationic Lipids." Il Farmaco, 2004, vol. 59, No. 11, pp. 869-878.

Arpicco S.et al., "Preparation and Characterization of Novel Cationic Lipids Developed for Gene Transfection." Proceed. Int'l. Symp. Control Rel. Bioact. Mater. 1999, vol. 26, pp. 759-760.

Beale, G., et al. "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Brummelkamp, et al. "A System for Stable Expression of Short Interfering RNAs in Mammalian Cells," Science, 2002, vol. 296, pp. 550-553.

Cevc, G., "How Membrane Chain-Melting Phase-Transition Temperature is Affected by Lipid CHain Asymmetry and Degree of Unsaturation: An Effective Chain Length Model." Biochemistry, 1991, vol. 30, No. 29, pp. 7186-7193. (ISSN 0006-2960).

Keough, K.M.W., "Influence of Chain Unsaturation and Chain Position on Thermotropism and Intermolecular Interactions in Membranes." Biochem. Soc. Transactions, 1990, vol. 18, No. 5, pp. 835-837. (ISSN 0300-5127).

Mashek et al. "Short Communication: Net Uptake of Nonesterified Long Chain Fatty Acids by the Perfused Caudate Lobe of the Caprine Liver," J. Dairy Sci., 2003, 86:1218-1220.

Vigh et al. "Does the membrane's physical state control the expression of heat shock and other genes?" TIBS, 1998, 23:369-374.

\* cited by examiner

DLenDMA.

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence:
      anti-luciferase siRNA sense sequence

<400> SEQUENCE: 1
gauuaugucc gguuauguau u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:
      anti-luciferase siRNA antisense sequence

<400> SEQUENCE: 2
uacauaaccg gacauaaucu u                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:sequence
      complementary to DNA target

<400> SEQUENCE: 3
gattatgtcc ggttatgtat t                                              21
```

CATIONIC LIPIDS AND METHODS OF USE

CROSS-REFERENCES TO RELATED APPLICATIONS

This application claimed the benefit of U.S. Provisional Patent Application Nos. 60/578,075 filed Jun. 7, 2004, 60/610,746, filed Sep. 17, 2004, and 60/679,427, filed May 9, 2005, the disclosures of each of which is incorporated by reference in its entirety for all purposes.

BACKGROUND OF THE INVENTION

An effective and safe gene delivery system is required for gene therapy to be clinically useful. Viral vectors are relatively efficient gene delivery systems, but suffer from a variety of limitations, such as the potential for reversion to the wild type as well as immune response concerns. As a result, nonviral gene delivery systems are receiving increasing attention (Worgall, et al., *Human Gene Therapy* 8:37-44 (1997); Peeters, et al., *Human Gene Therapy* 7:1693-1699 (1996); Yei, et al., *Gene Therapy* 1:192-200 (1994); Hope, et al., *Molecular Membrane Biology* 15:1-14 (1998)). Plasmid DNA-cationic liposome complexes are currently the most commonly employed nonviral gene delivery vehicles (Felgner, *Scientific American* 276:102-106 (1997); Chonn, et al., *Current Opinion in Biotechnology* 6:698-708 (1995)). However, complexes are large, poorly defined systems that are not suited for systemic applications and can elicit considerable toxic side effects (Harrison, et al., *Biotechniques* 19:816-823 (1995); Huang, et al., *Nature Biotechnology* 15:620-621 (1997); Templeton, et al., *Nature Biotechnology* 15:647-652 (1997); Hofland, et al., *Pharmaceutical Research* 14:742-749 (1997)).

Recent work has shown that plasmid DNA can be encapsulated in small (~70 nm diameter) "stabilized plasmid-lipid particles" (SPLP) that consist of a single plasmid encapsulated within a bilayer lipid vesicle (Wheeler, et al., *Gene Therapy* 6:271-281 (1999)). These SPLPs typically contain the "fusogenic" lipid dioleoylphosphatidyl-ethanolamine (DOPE), low levels of cationic lipid, and are stabilized in aqueous media by the presence of a poly(ethylene glycol) (PEG) coating. SPLP have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLP containing the luciferase marker gene are superior to the levels that can be achieved employing plasmid DNA-cationic liposome complexes (lipoplexes) or naked DNA. Still, improved levels of expression may be required for optimal therapeutic benefit in some applications (see, e.g., Monck, et al., *J. Drug Targ.* 7:439-452 (2000)).

Typically, both liposomes and SPLPs comprise cationic lipids. Often the cationic lipids have 2 alkyl chains, ether (oxygen) bonds, and an amine head group such as, e.g., DODAC and DODMA. Typically the alkyl chains comprise a single site of unsaturation. Unfortunately, cationic lipids with only a single site of unsaturation can lack flexibility. Liposomes or SPLP comprising these cationic lipids can lack sufficient membrane fluidity, thus impacting the efficiency of delivery of a bioactive agent to a cell or to a patient.

Lipid flexibility is important in the development of liposomal or SPLP drug delivery systems. Therefore, it is desirable to develop cationic lipids that are more flexible, thereby, increasing the membrane fluidity of the liposomes or the SPLP. The present invention addresses this and other needs.

SUMMARY OF THE INVENTION

The present invention provides novel cationic lipids that have increased flexibility over commonly used cationic lipids (such as DODAC and DODMA). More particularly, it has surprisingly been found that the cationic lipids of the present invention enhance the properties of liposomes as well as nucleic acid-lipid particles (SPLPs) by increasing the membrane fluidity of the liposome or SPLP, thus increasing the efficiency of delivery of bioactive agents in the liposomes and SPLP. In particular, the present invention provides compounds of Formula I having the following structure:

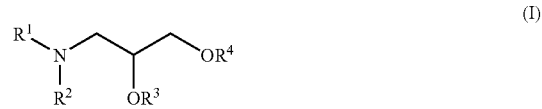

(I)

In the compounds of Formula I, above, $R^1$ and $R^2$ are independently and are H or $C_1$-$C_3$ alkyls. $R^3$ and $R^4$ are independently selected in the compounds of Formula I, and are alkyl groups having from about 10 to about 20 carbon atoms, and at least one of $R^3$ and $R^4$ comprises at least two sites of unsaturation. $R^3$ and $R^4$ may be the same or different. If different, $R^3$ and $R^4$ can differ either in terms of the alkyl chain length, in terms of the site of unsaturation, or in terms of the number of sites of unsaturation. $R^3$ and $R^4$ may comprise at least two sites of unsaturation (e.g., $R^3$ and $R^4$ may be, for example, dodecadienyl, tetradecadienyl, hexadecadienyl, linoleyl, and icosadienyl. In a preferred embodiment, $R^3$ and $R^4$ are both linoleyl. $R^3$ and $R^4$ may comprise at least three sites of unsaturation (e.g., $R^3$ and $R^4$ may be, for example, dodecatrienyl, tetradectrienyl, hexadecatrienyl, linolenyl, and icosatrienyl).

The present invention also provides compound of Formula II having the following structure:

(II)

In Formula II, above, $R^1$ and $R^2$ are independently selected and are H or $C_1$-$C_3$ alkyls. $R^3$ and $R^4$ are independently selected and are alkyl groups having from about 10 to about 20 carbon atoms, wherein at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

In another aspect, the present invention provides a liposome, the liposome comprising a cationic lipid of Formula I, Formula II, or a combination thereof. The liposome may further comprise a PEG-lipid (e.g., a PEG-diacylglycerol, a PEG-dialkyloxypropyl, a PEG-ceramide, a PEG-phosphatidylethanolamine, or mixtures thereof). The liposome can be empty or, alternatively, the liposome can further comprise one or more bioactive agents. Suitable bioactive agents include, but are not limited to, antineoplastic agents, antibiotics, immunomodulators, anti-inflammatory agents and agents acting on the central nervous system. Similarly, suitable bioactive agents include, but are not limited to, peptides, proteins and nucleic acids (e.g., single or double stranded DNA, singled stranded or double stranded RNA, including siRNA).

In another aspect the present invention provides a method of delivering a bioactive agent to a cell, the methods comprising contacting the cell with a liposome comprising a cationic lipid of Formula I, Formula II, or a combination thereof, wherein the bioactive agent is encapsulated in the liposome. Similarly, in another aspect, the present invention provides a method of delivering a bioactive agent to a patient, the method comprising administering to the patient a liposome comprising a cationic lipid of Formula I, Formula II, or a combination thereof, wherein the bioactive agent is encapsulated in the liposome.

In another aspect, the present invention provides a nucleic acid-lipid particle, the nucleic acid-lipid particle comprising: a nucleic acid; cationic lipid of Formula I, Formula II, or a combination thereof; a non-cationic lipid; and a PEG-lipid conjugate.

In yet another aspect, the present invention provides a method of introducing a nucleic acid into a cell, the method comprising contacting the cell with a nucleic acid-lipid particle comprising a cationic lipid of Formula I, Formula II, or a combination thereof, a non-cationic lipid, a PEG-lipid conjugate, and a nucleic acid.

Other features, objects and advantages of the invention and its preferred embodiments will become apparent from the detailed description, examples, claims and figures that follow.

DETAILED DESCRIPTION OF THE INVENTION

I. Introduction

Figure 1:
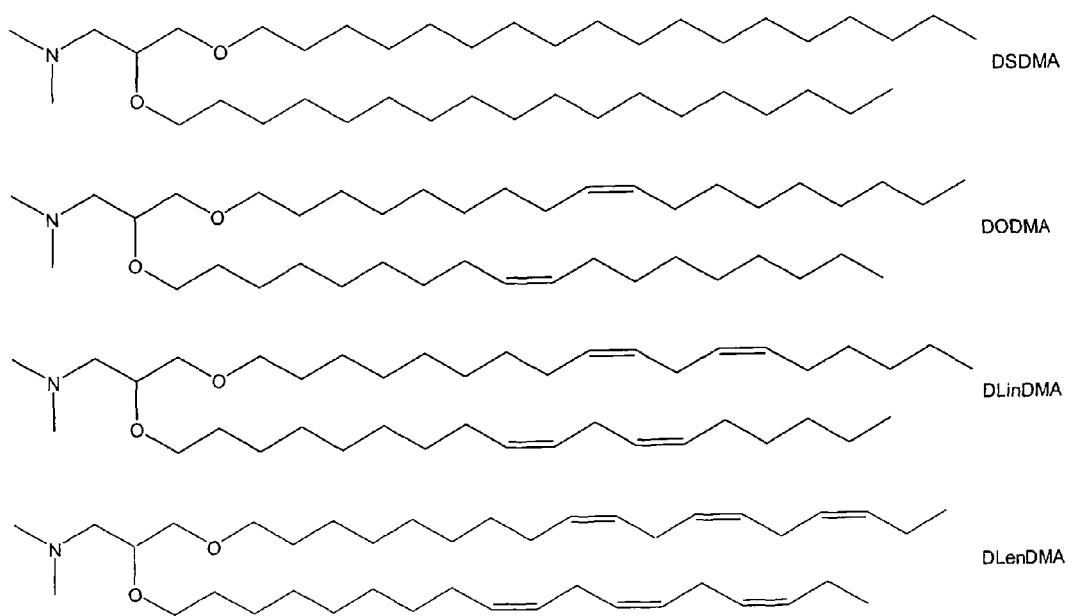
FIG. 1 illustrates the structures of two exemplary cationic lipids of the invention: 1,2-DiLinoleyloxy-N,N-dimethylaminopropane (DLinDMA) and 1,2-Dilinolenyloxy-N,N-dimethylaminopropane (DLenDMA).
Figure 2:
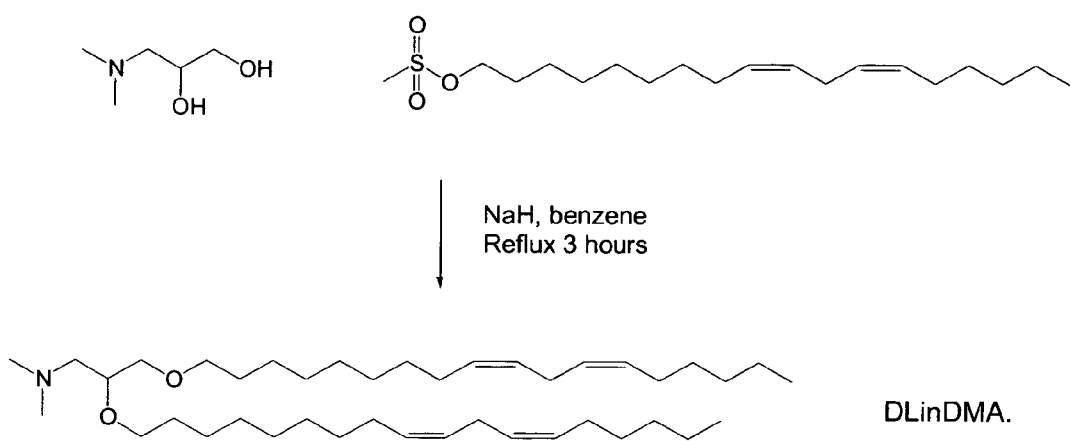
FIG. 2 illustrates the synthetic scheme for DLinDMA.
Figure 3:
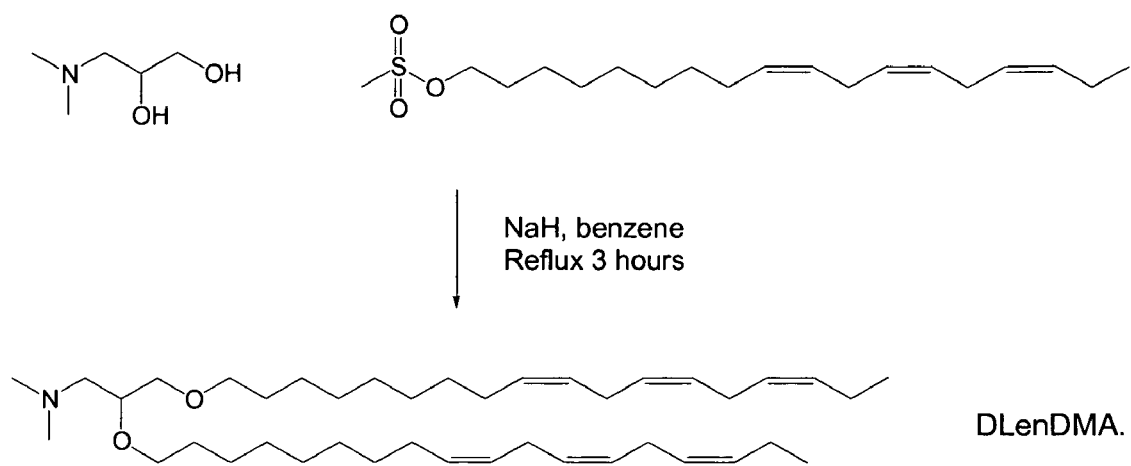
FIG. 3 illustrates the synthetic scheme for DLenDMA.
Figure 4:
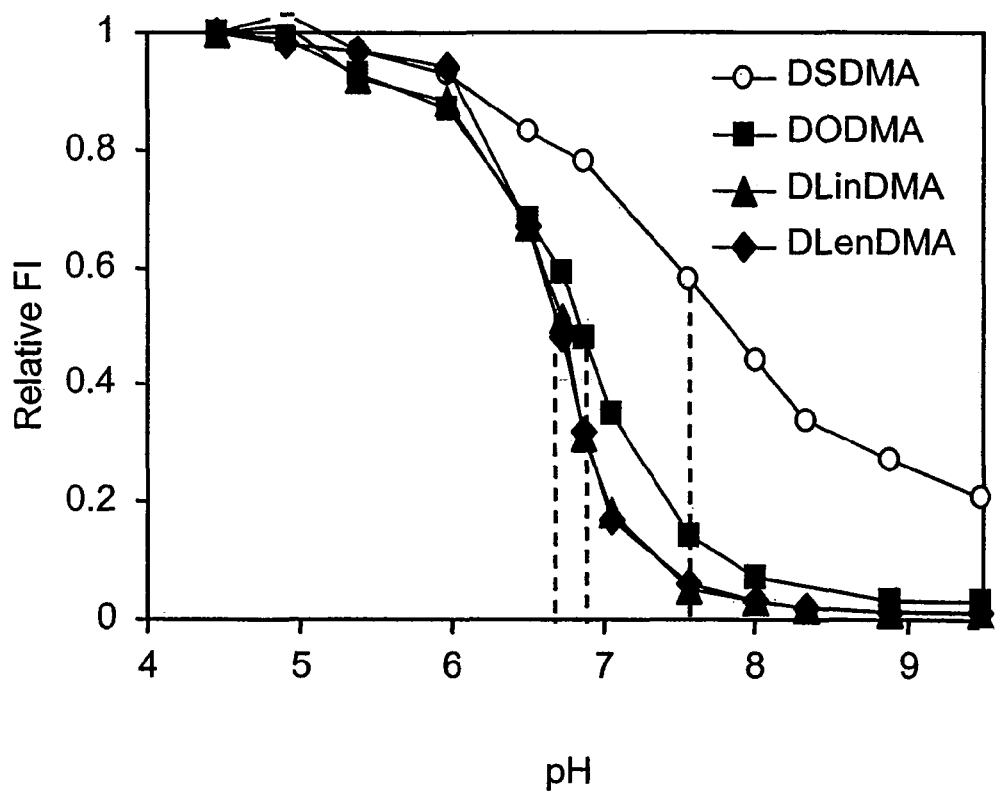
FIG. 4 illustrates data showing the apparent pKa of the cationic lipid incorporated in SNALP.

The present invention provides novel cationic lipids that have increased flexibility over commonly used cationic lipids (such as DODAC and DODMA). When incorporated into lipid vesicles (e.g., liposomes, SPLP, and SNALP), the cationic lipids described herein confer enhanced fusogenicity.

II. Definitions

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound with full encapsulation, partial encapsulation, or both. In a preferred embodiment, the nucleic acid is fully encapsulated in the lipid formulation (e.g., to form an SPLP, pSPLP, or other SNALP).

As used herein, the term "SNALP" refers to a stable nucleic acid lipid particle, including SPLP. A SNALP represents a vesicle of lipids coating a reduced aqueous interior comprising a nucleic acid (e.g., ssDNA, dsDNA, ssRNA, micro RNA (miRNA), short hairpin RNA (shRNA), dsRNA, siRNA, or a plasmid, including plasmids from which an interfering RNA is transcribed). As used herein, the term "SPLP" refers to a nucleic acid lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site and can mediate expression of the transfected gene at these distal sites. SPLPs include "pSPLP" which comprise an encapsulated condensing agent-nucleic acid complex as set forth in WO 00/03683.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SNALPs, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, and PEG conjugated to ceramides (see, U.S. Pat. No. 5,885,613). PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. Such lipids include, but are not limited to 1,2-DiLinoleyloxy-N,N-dimethylaminopropane ("DLinDMA"), 1,2-Dilinolenyloxy-N,N-dimethylaminopropane ("DLenDMA"), dioctadecyldimethylammonium ("DODMA"), Distearyldimethylammonium ("DSDMA"), N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). For example, cationic lipids that have a positive charge at below physiological pH include, but are not limited to: DODAP, DODMA, and DMDMA. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may comprise ether linkages and pH titratable head groups. Such lipids include, e.g., DODMA.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "nucleic acid" or "polynucleotide" refers to a polymer containing at least two deoxyribonucleotides or ribonucleotides in either single- or double-stranded form. Nucleic acids include nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. Nucleotides include chemically modified nucleotides as described in, e.g., WO 03/74654. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. The term nucleic acid is used interchangeably with gene, plasmid, cDNA, mRNA, and an interfering RNA molecule (e.g. a synthesized siRNA or an siRNA expressed from a plasmid).

III. Cationic Lipids

The present invention provides novel cationic lipids that have increased flexibility over commonly used cationic lipids (such as DODAC and DODMA). More particularly, the present invention provides novel cationic lipids of Formula I having the following structure:

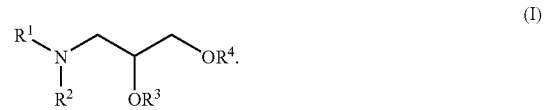

In Formula I, above, $R^1$ and $R^2$ are independently selected and are H or $C_1$-$C_3$ alkyls. $R^3$ and $R^4$ are independently selected and are alkyl groups having from about 10 to about 20 carbon atoms, wherein at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The present invention also provides novel cationic lipids of Formula II having the following structure:

In Formula II, above, $R^1$ and $R^2$ are independently selected and are H or $C_1$-$C_3$ alkyls. $R^3$ and $R^4$ are independently selected and are alkyl groups having from about 10 to about 20 carbon atoms; at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

IV. Lipid-Based Carrier Systems Containing Cationic Lipids

In one embodiment, the present invention provides stabilized nucleic acid-lipid particles (SPLPs or SNALPs) and other lipid-based carrier systems (e.g., a liposome, a micelle, a virosome, a lipid-nucleic acid particle, a nucleic acid complex and mixtures thereof) containing cationic lipids of the present invention, i.e., cationic lipids of Formula I, Formula II, or a combination thereof. The lipid-nucleic acid particles of the present invention typically comprise a nucleic acid, a cationic lipid of Formula I or Formula II, a non-cationic lipid and a PEG-lipid conjugate. The cationic lipid of Formula I or Formula II typically comprises from about 2% to about 60%, from about 5% to about 50%, from about 10% to about 45%, from about 20% to about 40%, or about 30% of the total lipid present in said particle. The non-cationic lipid typically comprises from about 5% to about 90%, from about 10% to about 85%, from about 20% to about 80%, from about 30% to about 70%, from about 40% to about 60% or about 48% of the total lipid present in said particle. The PEG-lipid conjugate typically comprises from about 1% to about 20%, from about 1.5% to about 18%, from about 4% to about 15%, from about 5% to about 12%, or about 2% of the total lipid present in said particle. The nucleic acid-lipid particles of the present invention may further comprise cholesterol. If present, the cholesterol typically comprises from about 10% to about 60%, from about 12% to about 58%, from about 20% to about 55%, or about 48% of the total lipid present in said particle. It will be readily apparent to one of skill in the art that the proportions of the components of the nucleic acid-lipid particles may be varied, e.g., using the ERP assay described herein. For example for systemic delivery, the cationic lipid may comprise from about 5% to about 15% of the total lipid present in said particle and for local or regional delivery, the cationic lipid comprises from about 40% to about 50% of the total lipid present in said particle.

The nucleic acid-lipid particles of the present invention typically have a mean diameter of about 50 nm to about 150 nm, more typically about 100 nm to about 130 nm, most typically about 110 nm to about 115 nm, and are substantially nontoxic. In addition, the nucleic acids when present in the nucleic acid-lipid particles s of the present invention are resistant to aqueous solution to degradation with a nuclease. Nucleic acid-lipid particles and their method of preparation are disclosed in U.S. Pat. Nos. 5,753,613; 5,785,992; 5,705,385; 5,976,567; 5,981,501; 6,110,745; 6,320,017 and WO 96/40964.

A. Cationic Lipids

Cationic lipids of Formula I and II may be used in the present invention, either alone or in combination with one or more other cationic lipid species or non-cationic lipid species.

The cationic lipids of Formula I and Formula II described herein typically carry a net positive charge at a selected pH, such as physiological pH. It has been surprisingly found that cationic lipids comprising alkyl chains with multiple sites of unsaturation, e.g., at least two or three sites of unsaturation, are particularly useful for forming lipid-nucleic acid particles with increased membrane fluidity. A number of cationic lipids and related analogs, which are also useful in the present invention, have been described in co-pending U.S. Ser. No. 08/316,399; U.S. Pat. Nos. 5,208,036, 5,264,618, 5,279,833 and 5,283,185, and WO 96/10390.

Additional suitable cationic lipids include, e.g., dioctadecyldimethylammonium ("DODMA"), Distearyldimethylammonium ("DSDMA"), N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). A number of these lipids and related analogs, which are also useful in the present invention, have been described in U.S. Pat. Nos. 5,208,036, 5,264,618, 5,279,833, 5,283,185, 5,753,613 and 5,785,992.

B. Non-Cationic Lipids

The noncationic lipids used in the present invention can be any of a variety of neutral uncharged, zwitterionic or anionic lipids capable of producing a stable complex. They are preferably neutral, although they can alternatively be positively or negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429.

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will be cholesterol, 1,2-sn-dioleoylphosphatidylethanolamine, or egg sphingomyelin (ESM).

C. Bilayer Stabilizing Component

In addition to cationic and non-cationic lipids, the SPLPs of the present invention comprise bilayer stabilizing component (BSC) such as an ATTA-lipid or a PEG-lipid, such as PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689), PEG coupled to phosphatidylethanolamine (PE) (PEG-PE), or PEG conjugated to ceramides, or a mixture thereof (see, U.S. Pat. No. 5,885,613). In one preferred embodiment, the BSC is a conjugated lipid that inhibits aggregation of the SPLPs. Suitable conjugated lipids include, but are not limited to PEG-lipid conjugates, ATTA-lipid conjugates, cationic-polymer-lipid conjugates (CPLs) or mixtures thereof. In one preferred embodiment, the SPLPs comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

In a preferred embodiment, the PEG has an average molecular weight of from about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of C$_{10}$ to C$_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidylethanolamine (DSPE).

The term "ATTA" or "polyamide" refers to, but is not limited to, compounds disclosed in U.S. Pat. Nos. 6,320,017 and 6,586,559. These compounds include a compound having the formula

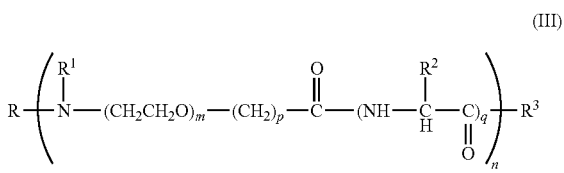

(III)

wherein: R is a member selected from the group consisting of hydrogen, alkyl and acyl; R$^1$ is a member selected from the group consisting of hydrogen and alkyl; or optionally, R and R$^1$ and the nitrogen to which they are bound form an azido moiety; R$^2$ is a member of the group selected from hydrogen, optionally substituted alkyl, optionally substituted aryl and a side chain of an amino acid; R$^3$ is a member selected from the group consisting of hydrogen, halogen, hydroxy, alkoxy, mercapto, hydrazino, amino and NR$^4$R$^5$, wherein R$^4$ and R$^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2-fatty acyl chains, R$^1$ and R$^2$, both of which have independently between 2 and 30 carbons bonded to the 1- and 2-position of glycerol by ester linkages. The acyl groups can be saturated or have varying degrees of unsaturation. Diacylglycerols have the following general formula:

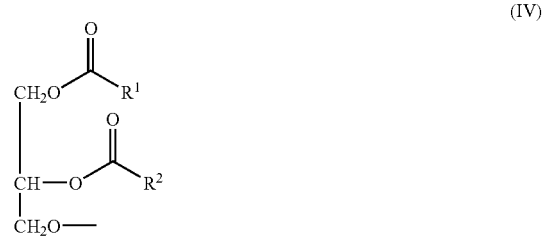

(IV)

The term "dialkyloxypropyl" refers to a compound having 2-alkyl chains, R$^1$ and R$^2$, both of which have independently between 2 and 30 carbons. The alkyl groups can be saturated or have varying degrees of unsaturation. Dialkyloxypropyls have the following general formula:

(V)

In one preferred embodiment, the PEG-lipid is a PEG-DAA conjugate has the following formula:

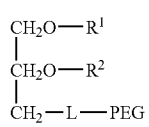

(VI)

In Formula VI, $R^1$ and $R^2$ are independently selected and are long-chain alkyl groups having from about 10 to about 22 carbon atoms. The long-chain alkyl groups can be saturated or unsaturated. Suitable alkyl groups include, but are not limited to, lauryl (C12), myristyl (C14), palmityl (C16), stearyl (C18) and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, "$R^1$ and $R^2$" are independently selected and are alkyl groups having from about 10 to about 20 carbon atoms; PEG is a polyethyleneglycol; and L is a non-ester-containing linker moiety as described above. Suitable alkyl groups include, but are not limited to, lauryl (C12), myristyl (C14), palmityl (C16), stearyl (C18) and icosyl (C20). In a preferred embodiment; $R^1$ and $R^2$ are the same, i.e., they are both myristyl (C14) or both palmityl (C16) or both stearyl (C18). In a preferred embodiment, the alkyl groups are saturated.

In Formula VI above, "PEG" is a polyethylene glycol having an average molecular weight ranging of about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted with alkyl, alkoxy, acyl or aryl. In a preferred embodiment, the terminal hydroxyl group is substituted with a methoxy or methyl group.

In Formula VI, above, "L" is a non-ester containing linker moiety or an ester containing linker moiety. In a preferred embodiment, L is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Furniss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

In a presently preferred embodiment, the PEG-DAA conjugate is a dilauryloxypropyl (C12)-PEG conjugate, dimyristyloxypropyl (C14)-PEG conjugate, a dipalmitoyloxypropyl (C16)-PEG conjugate or a disteryloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

In addition to the foregoing components, the SNALPs and SPLPs of the present invention can further comprise cationic poly(ethylene glycol) (PEG) lipids, or CPLs, that have been designed for insertion into lipid bilayers to impart a positive charge (see, Chen, et al., *Bioconj. Chem.* 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPL include compounds of Formula VII:

(VII)

wherein A, W and Y are as described below.

With reference to Formula VII, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

D. Products of Interest

In addition to the above components, the SPLPs and SNALPs of the present invention comprise a nucleic acid (e.g., single stranded or double stranded DNA, single stranded or double stranded RNA, RNAi, siRNA, and the like). Suitable nucleic acids include, but are not limited to, plasmids, antisense oligonucleotides, ribozymes as well as other poly- and oligonucleotides. In preferred embodiments, the nucleic acid encodes a product, e.g., a therapeutic product, of interest. The SPLP's and SNLPs of the present invention can be used to deliver the nucleic acid to a cell (e.g., a cell in a mammal) for, e.g., expression of the nucleic acid or for silencing of a target sequence expressed by the cell.

The product of interest can be useful for commercial purposes, including for therapeutic purposes as a pharmaceutical or diagnostic. Examples of therapeutic products include a protein, a nucleic acid, an antisense nucleic acid, ribozymes, tRNA, snRNA, siRNA, an antigen, Factor VIII, and Apoptin (Zhuang et al. (1995) *Cancer Res.* 55(3): 486-489). Suitable classes of gene products include, but are not limited to, cytotoxic/suicide genes, immunomodulators, cell receptor ligands, tumor suppressors, and anti-angiogenic genes. The particular gene selected will depend on the intended purpose or treatment. Examples of such genes of interest are described below and throughout the specification.

In some embodiments, the nucleic acid is an siRNA molecule that silences the gene of interest. Such nucleic acids can be administered alone or in combination with the administration of conventional agents used to treat the disease or disorder associated with the gene of interest. In other embodiments, the nucleic acid encodes a polypeptide expressed or overexpressed in a subject with a particular disease or disorder (e.g., a pathogenic infection or a neoplastic disorder) and can conveniently be used to generate an immune response against the polypeptide expressed by the gene. Such nucleic acids can be administered alone or in combination with the administration of conventional agents used to treat the disease or disorder. In even other embodiments, the nucleic acid encodes a polypeptide that is underexpressed or not expressed in subjects with a particular disease or disorder (e.g., a metabolic disease or disorder) and can conveniently be used to express the polypeptides and can be administered alone or in combination with the administration of conventional agents used to treat the disease or disorder.

1. Genes of Interest

Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes, such as those associated with inflammatory and autoimmune responses, ligand receptor genes, and genes associated with neurodegenerative disorders.

a) Genes associated with Viral Infection and Survival

Genes associated with viral infection and survival include those expressed by a virus in order to bind, enter and replicate in a cell. Of particular interest are viral sequences associated with chronic viral diseases. Viral sequences of particular interest include sequences of Hepatitis viruses (Hamasaki, et al., *FEBS Lett.* 543:51 (2003); Yokota, et al., *EMBO Rep.* 4:602 (2003); Schlomai, et al., *Hepatology* 37:764 (2003); Wilson, et al., *Proc. Natl. Acad. Sci.* 100:2783 (2003); Kapadia, et al., *Proc. Natl. Acad. Sci.* 100:2014 (2003); and FIELDS VIROLOGY (Knipe et al. eds. 2001)), Human Immunodeficiency Virus (HIV) (Banerjea, et al., *Mol. Ther.* 8:62 (2003); Song, et al., *J. Virol.* 77:7174 (2003); Stephenson *JAMA* 289: 1494 (2003); Qin, et al., *Proc. Natl. Acad. Sci.* 100:183 (2003)), Herpes viruses (Jia, et al., *J. Virol.* 77:3301 (2003)), and Human Papilloma Viruses (HPV) (Hall, et al., *J. Virol.* 77:6066 (2003); Jiang, et al., *Oncogene* 21:6041 (2002)). Exemplary hepatitis viral nucleic acid sequences that can be silenced include, but are not limited to: nucleic acid sequences involved in transcription and translation (e.g., En1, En2, X, P), nucleic acid sequences encoding structural proteins (e.g., core proteins including C and C-related proteins; capsid and envelope proteins including S, M, and/or L proteins, or fragments thereof) (see, e.g., FIELDS VIROLOGY, 2001, supra). Exemplary Hepatitis C nucleic acid sequences that can be silenced include, but are not limited to: serine proteases (e.g., NS3/NS4), helicases (e.g. NS3), polymerases (e.g., NS5B), and envelope proteins (e.g., E1, E2, and p7). Hepatitis A nucleic acid sequences are set forth in e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in e.g., Genbank Accession No. NC_001434; and Hepatitis G nucleic acid sequences are set forth in e.g., Genbank Accession No. NC_001710.

b) Genes Associated with Metabolic Diseases and Disorders

Genes associated with metabolic diseases and disorders (e.g., disorders in which the liver is the target and liver diseases and disorders) include, for example genes expressed in, for example, dyslipidemia (e.g., liver X receptors (e.g., LXRα and LXRβ Genback Accession No. NM_007121), farnesoid X receptors (FXR) (Genbank Accession No. NM_005123), sterol-regulatory element binding protein (SREBP), Site-1 protease (S1P), 3-hydroxy-3-methylglutaryl coenzyme-A reductase (HMG coenzyme-A reductase), Apolipoprotein (ApoB), and Apolipoprotein (ApoE)) and diabetes (e.g., Glucose 6-phosphatase) (see, e.g., Forman et al., *Cell* 81:687 (1995); Seol et al., *Mol. Endocrinol.* 9:72 (1995), Zavacki et al., *PNAS USA* 94:7909 (1997); Sakai, et al., *Cell* 85:1037-1046 (1996); Duncan, et al., *J. Biol. Chem.* 272:12778-12785 (1997); Willy, et al., *Genes Dev.* 9(9):1033-45 (1995); Lehmann, et al., *J. Biol. Chem.* 272(6):3137-3140 (1997); Janowski, et al., *Nature* 383:728-731 (1996); Peet, et al., *Cell* 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues.

c) Genes Associated with Tumorigenesis

Examples of gene sequences associated with tumorigenesis and cell transformation include translocation sequences such as MLL fusion genes, BCR-ABL (Wilda, et al., *Oncogene*, 21:5716 (2002); Scherr, et al., *Blood* 101:1566), TEL-AML1, EWS-FLI1, TLS-FUS, PAX3-FKHR, BCL-2, AML1-ETO and AML1-MTG8 (Heidenreich, et al., *Blood* 101:3157 (2003)); overexpressed sequences such as multidrug resistance genes (Nieth, et al., *FEBS Lett.* 545:144 (2003); Wu, et al, *Cancer Res.* 63:1515 (2003)), cyclins (Li, et al., *Cancer Res.* 63:3593 (2003); Zou, et al., *Genes Dev.* 16:2923 (2002)), beta-Catenin (Verma, et al., *Clin Cancer Res.* 9:1291 (2003)), telomerase genes (Kosciolek, et al., *Mol Cancer Ther.* 2:209 (2003)), c-MYC, N-MYC, BCL-2, ERBB1 and ERBB2 (Nagy, et al. *Exp. Cell Res.* 285:39 (2003)); and mutated sequences such as RAS (reviewed in Tuschl and Borkhardt, *Mol. Interventions*, 2:158 (2002)). For example, silencing of sequences that encode DNA repair enzymes find use in combination with the administration of chemotherapeutic agents (Collis, et al., *Cancer Res.* 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a gene sequence of interest.

d) Angiogenic/Anti-Angiogenic Genes

Angiogenic genes are able to promote the formation of new vessels. Of particular interest is Vascular Endothelial Growth Factor (VEGF) (Reich, et al., *Mol. Vis.* 9:210 (2003)) or VEGFr. siRNA sequences that target VEGFr are set forth in, e.g., GB 2396864; U.S. Patent Publication No. 20040142895; and CA2456444.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see e.g., U.S. Pat. No. 6,174,861), angiostatin (see, e.g., U.S. Pat. No. 5,639,725), and VEGF-R2 (see e.g., Decaussin et al. (1999) *J. Pathol.* 188(4): 369-737).

e) Immonomodulator Genes

Immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, SCF, etc.), interleukins (e.g., IL-2, IL-3, IL-4, IL-6, IL-7, IL-10, IL-12, IL-15, IL-20, etc.), interferons (e.g., IFN-α, IFN-β, IFN-γ, etc.), TNF (e.g., TNF-α), and Flt3-Ligand. Fas and Fas Ligand genes are also immunomodulator target sequences of interest (Song, et al., *Nat. Med.* 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., *FEBS Lett.* 527:274 (2002)).

f) Cell Receptor Ligands

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., *Hum. Mol. Genet.* 11:175 (2002)).

g) Tumor Suppressor Genes

Tumor suppressor genes are genes that are able to inhibit the growth of a cell, particularly tumor cells. Thus, delivery of these genes to tumor cells is useful in the treatment of cancers. Tumor suppressor genes include, but are not limited to, p53. (Lamb et al., *Mol. Cell. Biol.* 6:1379-1385 (1986), Ewen et al., *Science* 255:85-87 (1992), Ewen et al. (1991) *Cell* 66:1155-1164, and Hu et al., *EMBO J.* 9:1147-1155 (1990)), RB1 (Toguchida et al. (1993) *Genomics* 17:535-543), WT1 (Hastie, N. D., *Curr. Opin. Genet. Dev.* 3:408-413 (1993)), NF1 (Trofatter et al., *Cell* 72:791-800 (1993), Cawthon et al., *Cell* 62:193-201 (1990)), VHL (Latif et al., *Science* 260: 1317-1320 (1993)), APC (Gorden et al., *Cell* 66:589-600 (1991)), DAP kinase (see e.g., Diess et al. (1995) *Genes Dev.* 9: 15-30), p16 (see e.g., Marx (1994) *Science* 264(5167): 1846), ARF (see e.g., Quelle et al. (1995) *Cell* 83(6): 993-1000), Neurofibromin (see e.g., Huynh et al. (1992) *Neurosci. Lett.* 143 (1-2): 233-236), and PTEN (see e.g., Li et al. (1997) *Science* 275(5308): 1943-1947).

h) Cytotoxic/Suicide Genes

Cytotoxic/suicide genes are those genes that are capable of directly or indirectly killing cells, causing apoptosis, or arresting cells in the cell cycle. Such genes include, but are not limited to, genes for immunotoxins, a herpes simplex virus thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, and a cytochrome P450 2B1.

In a gene therapy technique known as gene-delivered enzyme prodrug therapy ("GDEPT") or, alternatively, the "suicide gene/prodrug" system, agents such as acyclovir and ganciclovir (for thymidine kinase), cyclophosphoamide (for cytochrome P450 2B1), 5-fluorocytosine (for cytosine deaminase), are typically administered systemically in conjunction (e.g., simultaneously or nonsimultaneously, e.g., sequentially) with a expression cassette encoding a suicide gene compositions of the present invention to achieve the desired cytotoxic or cytostatic effect (see, e.g., Moolten, F. L., *Cancer Res.*, 46:5276-5281 (1986)). For a review of the GDEPT system, see, Moolten, F. L., *The Internet Book of Gene Therapy, Cancer Therapeutics*, Chapter 11 (Sobol, R. E., Scanlon, N J (Eds) Appelton & Lange (1995)). In this method, a heterologous gene is delivered to a cell in an expression cassette containing a RNAP promoter, the heterologous gene encoding an enzyme that promotes the metabolism of a first compound to which the cell is less sensitive (i.e., the "prodrug") into a second compound to which is cell is more sensitive. The prodrug is delivered to the cell either with the gene or after delivery of the gene. The enzyme will process the prodrug into the second compound and respond accordingly. A suitable system proposed by Moolten is the herpes simplex virus-thymidine-kinase (HSV-TK) gene and the prodrug ganciclovir. This method has recently been employed using cationic lipid-nucleic aggregates for local delivery (i.e., direct intra-tumoral injection), or regional delivery (i.e., intra-peritoneal) of the TK gene to mouse tumors by Zerrouqui, et al., *Can. Gen. Therapy*, 3(6):385-392 (1996); Sugaya, et al., *Hum. Gen. Ther.*, 7:223-230 (1996) and Aoki, et al., *Hum. Gen. Ther.*, 8:1105-1113 (1997). Human clinical trials using a GDEPT system employing viral vectors have been proposed (see, *Hum. Gene Ther.*, 8:597-613 (1997), and *Hum. Gene Ther.*, 7:255-267 (1996)) and are underway.

Any suicide gene/prodrug combination can be used in accordance with the present invention. Several suicide gene/prodrug combinations suitable for use in the present invention are cited in Sikora, K. in OECD Documents, Gene Delivery Systems at pp. 59-71 (1996), include, but are not limited to, the following:

| Suicide Gene Product | Less Active ProDrug | Activated Drug |
|---|---|---|
| Herpes simplex virus type 1 thymidine kinase (HSV-TK) | ganciclovir(GCV), acyclovir, bromovinyl-deoxyuridine, or other substrates | phosphorylated dGTP analogs |
| Cytosine Deaminase (CD) | 5-fluorocytosine | 5-fluorouracil |
| Xanthine-guanine-phosphoribosyl transferase (XGPRT) | 6-thioxanthine (6TX) | 6-thioguano-sinemonophosphate |
| Purine nucleoside phosphorylase | MeP-dr | 6-methylpurine |
| Cytochrome P450 2B1 | cyclophosphamide | [cytotoxic metabolites] |
| Linamarase | amygdalin | cyanide |
| Nitroreductase | CB 1954 | nitrobenzamidine |
| Beta-lactamase | PD | PD mustard |
| Beta-glucuronidase | adria-glu | adriamycin |
| Carboxypeptidase | MTX-alanine | MTX |
| Glucose oxidase | glucose | peroxide |
| Penicillin amidase | adria-PA | adriamycin |
| Superoxide dismutase | XRT | DNA damaging agent |
| Ribonuclease | RNA | cleavage products |

Any prodrug can be used if it is metabolized by the heterologous gene product into a compound to which the cell is more sensitive. Preferably, cells are at least 10-fold more sensitive to the metabolite than the prodrug.

Modifications of the GDEPT system that may be useful with the invention include, for example, the use of a modified TK enzyme construct, wherein the TK gene has been mutated to cause more rapid conversion of prodrug to drug (see, for example, Black, et al., *Proc. Natl. Acad. Sci, U.S.A.*, 93: 3525-3529 (1996)). Alternatively, the TK gene can be delivered in a bicistronic construct with another gene that enhances its effect. For example, to enhance the "bystander effect" also known as the "neighbor effect" (wherein cells in the vicinity of the transfected cell are also killed), the TK gene can be delivered with a gene for a gap junction protein, such as connexin 43. The connexin protein allows diffusion of toxic products of the TK enzyme from one cell into another. The TK/Connexin 43 construct has a CMV promoter operably linked to a TK gene by an internal ribosome entry sequence and a Connexin 43-encoding nucleic acid.

2. siRNA

In some embodiments, the nucleic acid is an siRNA. The siRNA can be used to downregulate or silence the translation (i.e., expression) of a gene of interest. Suitable siRNA sequences can be identified using any means known in the art. Typically, the methods described in Elbashir, et al., *Nature* 411:494-498 (2001) and Elbashir, et al., *EMBO J.* 20: 6877-6888 (2001) are combined with rational design rules set forth in Reynolds et al., *Nature Biotech.* 22(3):326-330 (2004).

Typically, the sequence within about 50 to about 100 nucleotides 3' of the AUG start codon of a transcript from the target gene of interest is scanned for dinucleotide sequences (e.g., AA, CC, GG, or UU) (see, e.g., Elbashir, et al., *EMBO J.* 20: 6877-6888 (2001)). The nucleotides immediately 3' to the dinucleotide sequences are identified as potential siRNA target sequences. Typically, the 19, 21, 23, 25, 27, 29, 31, 33, 35 or more nucleotides immediately 3' to the dinucleotide sequences are identified as potential siRNA target sites. In some embodiments, the dinucleotide sequence is an AA sequence and the 19 nucleotides immediately 3' to the AA dinucleotide are identified as a potential siRNA target site. Typically siRNA target sites are spaced at different positions along the length of the target gene. To further enhance silencing efficiency of the siRNA sequences, potential siRNA target sites may be further analyzed to identify sites that do not contain regions of homology to other coding sequences. For example, a suitable siRNA target site of about 21 base pairs typically will not have more than 16-17 contiguous base pairs of homology to other coding sequences. If the siRNA sequences are to be expressed from an RNA Pol III promoter, siRNA target sequences lacking more than 4 contiguous A's or T's are selected.

Once the potential siRNA target site has been identified siRNA sequences complementary to the siRNA target sites may be designed. To enhance their silencing efficiency, the siRNA sequences may also be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA.

In some embodiments, once a potential siRNA sequence has been identified, the sequence is analyzed for the presence or absence of immunostimulatory motifs (e.g., GU-rich motifs) as described in, e.g., co-pending U.S. Provisional Patent Application Nos. 60/585,301, filed Jul. 2, 2004; 60/589,363, filed Jul. 19, 2004; 60/627,326, filed Nov. 12, 2004; and 60/665,297, filed Mar. 25, 2005. Once identified, the immunostimulatory siRNA molecules can be modified to increase or decrease their immunostimulatory properties and the non-immunostimulatory molecules can be modified so that they possess immunostimulatory properties 3. Generating siRNA siRNA can be provided in several forms including, e.g., as one or more isolated small-interfering RNA (siRNA) duplexes, longer double-stranded RNA (dsRNA) or as siRNA or dsRNA transcribed from a transcriptional cassette in a DNA plasmid. siRNA may also be chemically synthesized. Preferably, the synthesized or transcribed siRNA have 3' overhangs of about 1-4 nucleotides, preferably of about 2-3 nucleotides and 5' phosphate termini. The siRNA sequences may have overhangs (e.g., 3' or 5' overhangs as described in (Elbashir, et al., *Genes Dev.* 15:188 (2001); Nykänen, et al., *Cell* 107:309 (2001)) or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA); or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., *Science* 296:550 (2002); Donzé, et al., *Nucleic Acids Res.* 30:e46 (2002); Paddison, et al., *Genes Dev.* 16:948 (2002); Yu, et al., *Proc. Natl. Acad. Sci.* 99:6047 (2002); Lee, et al., *Nat. Biotech.* 20:500 (2002); Miyagishi, et al., *Nat. Biotech.* 20:497 (2002); Paul, et al., *Nat. Biotech.* 20:505 (2002); and Sui, et al., *Proc. Natl. Acad. Sci.* 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, *Science*, supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, *Gene* 25:263-269 (1983); Sambrook et al., supra; Ausubel et al., supra), as are PCR methods (see U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

A suitable plasmid is engineered to contain, in expressible form, a template sequence that encodes a partial length sequence or an entire length sequence of a gene product of interest. Template sequences can also be used for providing isolated or synthesized siRNA and dsRNA. Generally, it is desired to downregulate or silence the transcription and translation of a gene product of interest.

V. Preparation of Nucleic Acid-Lipid Particles

The present invention provides a method of preparing serum-stable nucleic acid-lipid particles in which the plasmid or other nucleic acid is encapsulated in a lipid bilayer and is protected from degradation. The particles made by the methods of this invention typically have a size of about 50 nm to about 150 nm, more typically about 100 nm to about 130 nm, most typically about 110 nm to about 115 nm. The particles can be formed by any method known in the art including, but not limited to: a continuous mixing method, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the noncationic lipids are ESM, DOPE, DOPC, DPPE, DMPE, 16:0 Monomethyl-Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine, DSPE, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is a lipid of Formula I or II or combinations thereof; the noncationic lipid is ESM, DOPE, PEG-DAAs, distearoylphosphatidylcholine (DSPC), cholesterol, or combinations thereof (e.g. DSPC and PEG-DAAs); and the organic solvent is methanol, chloroform, methylene chloride, ethanol, diethyl ether or combinations thereof.

In a particularly preferred embodiment, the present invention provides for nucleic acid-lipid particles produced via a continuous mixing method, e.g., process that includes providing an aqueous solution comprising a nucleic acid such as an siRNA or a plasmid, in a first reservoir, and providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process is described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, more typically about 100 nm to about 130 nm, most typically about 110 nm to about 115 nm. The particles thus formed do not aggregate and are optionally sized to achieve a uniform particle size.

In some embodiments, the particles are formed using detergent dialysis. Without intending to be bound by any particular mechanism of formation, a plasmid or other nucleic acid (e.g., siRNA) is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the plasmid or other nucleic acid is encapsulated in a lipid bilayer. Thus, the present invention provides a method for the preparation of serum-stable nucleic acid-lipid particles, comprising:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of nucleic acid in solution will typically be from about 25 μg/mL to about 1 mg/mL, preferably from about 25 μg/mL to about 200 μg/mL, and more preferably from about 50 μg/mL to about 100 μg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C. For nucleic acids which are particularly sensitive to temperature, the coated complexes can be formed at lower temperatures, typically down to about 4° C.

In a preferred embodiment, the nucleic acid to lipid ratios (mass/mass ratios) in a formed nucleic acid-lipid particle will range from about 0.01 to about 0.08. The ratio of the starting materials also falls within this range because the purification step typically removes the unencapsulated nucleic acid as well as the empty liposomes. In another preferred embodiment, the nucleic acid-lipid particle preparation uses about 400 μg nucleic acid per 10 mg total lipid or a nucleic acid to lipid ratio of about 0.01 to about 0.08 and, more preferably, about 0.04, which corresponds to 1.25 mg of total lipid per 50 μg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the non-cationic lipids will further comprise polyethylene glycol-based polymers such as PEG 2000, PEG 5000 and polyethylene glycol conjugated to a diacylglycerol, a ceramide or a phospholipid, as described in U.S. Pat. No. 5,820,873 and U.S. Patent Publication No. 20030077829. In further preferred embodiments, the non-cationic lipids will further comprise polyethylene glycol-based polymers such as PEG 2000, PEG 5000 and polyethylene glycol conjugated to a dialkyloxypropyl.

The amount of non-cationic lipid which is used in the present methods is typically about 2 to about 20 mg of total lipids to 50 μg of nucleic acid. Preferably the amount of total lipid is from about 5 to about 10 mg per 50 μg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, more typically about 100 nm to about 130 nm, most typically about 110 nm to about 115 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:
  (a) preparing a mixture comprising cationic-lipids and non-cationic lipids in an organic solvent;
  (b) contacting an aqueous solution of nucleic acid with said mixture in step (a) to provide a clear single phase; and
  (c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (or plasmids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, more typically about 100 nm to about 130 nm, most typically about 110 nm to about 115 nm. To achieve further size reduction or homogeneity of size in the particles, sizing can be conducted as described above.

In other embodiments, the methods will further comprise adding nonlipid polycations which are useful to effect the delivery to cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:
  (a) contacting nucleic acids with a solution comprising non-cationic lipids and a detergent to form a nucleic acid-lipid mixture;
  (b) contacting cationic lipids with the nucleic acid-lipid mixture to neutralize a portion of the negative charge of the nucleic acids and form a charge-neutralized mixture of nucleic acids and lipids; and
  (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and, DLenDMA. These lipids and related analogs have been described in U.S. Provisional Patent Application Nos. 60/578,075, filed Jun. 7, 2004; 60/610,746, filed Sep. 17, 2004; and 60/679,427, filed May 9, 2005.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, more typically about 50 nm to about 150 nm, even more typically about 100 nm to about 130 nm, most typically about 110 nm to about 115 nm. To achieve further size reduction or homogeneity of size in the particles, the nucleic acid-lipid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of nucleic acid-lipid particles, comprising:
(a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;
(b) contacting the hydrophobic, nucleic acid-lipid complex in solution with non-cationic lipids, to provide a nucleic acid-lipid mixture; and
(c) removing the organic solvents from the nucleic acid-lipid mixture to provide nucleic acid-lipid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DOPE, DOPC, polyethylene glycol-based polymers (e.g., PEG 2000, PEG 5000, PEG-modified diacylglycerols, or PEG-modified dialkyloxypropyls), distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine, DSPE, cholesterol, or combinations thereof. In still other preferred embodiments, the organic solvents are methanol, chloroform, methylene chloride, ethanol, diethyl ether or combinations thereof.

In one embodiment, the nucleic acid is a plasmid from which an interfering RNA is transcribed; the cationic lipid is DLindMA, DLenDMA, DODAC, DDAB, DOTMA, DOSPA, DMRIE, DOGS or combinations thereof; the non-cationic lipid is ESM, DOPE, DAG-PEGs, distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine DSPE, cholesterol, or combinations thereof (e.g. DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In yet another aspect, the present invention provides nucleic acid-lipid particles which are prepared by the methods described above. In these embodiments, the nucleic acid-lipid particles are either net charge neutral or carry an overall charge which provides the particles with greater gene lipofection activity. Preferably, the nucleic acid component of the particles is a nucleic acid which interferes with the production of an undesired protein. In a preferred embodiment, the nucleic acid comprises an interfering RNA, the non-cationic lipid is egg sphingomyelin and the cationic lipid is DLinDMA or DLenDMA. In a preferred embodiment, the nucleic acid comprises an interfering RNA, the non-cationic lipid is a mixture of DSPC and cholesterol, and the cationic lipid is DLinDMA or DLenDMA. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385, 6,586,410, 5,981,501 6,534,484; 6,852,334; U.S. Patent Publication No. 20020072121, as well as in WO 00/62813.

A. Administration of the Nucleic Acid-Lipid Particles

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

As described above, in some embodiments, the nucleic acid-lipid particles of the present invention comprise PEG-DAA conjugates. It is often desirable to include other components that act in a manner similar to the PEG-DAA conjugates and that serve to prevent particle aggregation and to provide a means for increasing circulation lifetime and increasing the delivery of the nucleic acid-lipid particles to the target tissues. Such components include, but are not limited to, PEG-lipid conjugates, such as PEG-diacylglycerols, PEG-ceramides or PEG-phospholipids (such as PEG-PE), ganglioside $G_{M1}$-modified lipids or ATTA-lipids to the particles. Typically, the concentration of the component in the particle will be about 1-20% and, more preferably from about 3-10%.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In another example of their use, lipid-nucleic acid particles can be incorporated into a broad range of topical dosage forms including, but not limited to, gels, oils, emulsions and the like. For instance, the suspension containing the nucleic acid-lipid particles can be formulated and administered as topical creams, pastes, ointments, gels, lotions and the like.

Once formed, the serum-stable nucleic acid-lipid particles of the present invention are useful for the introduction of nucleic acids into cells. Accordingly, the present invention also provides methods for introducing a nucleic acids (e.g., a plasmid or and siRNA) into a cell. The methods are carried out in vitro or in vivo by first forming the particles as described above and then contacting the particles with the cells for a period of time sufficient for delivery of the nucleic acid to the cell to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

Using the ERP assay of the present invention, the transfection efficiency of the SPLP or other lipid-based carrier system can be optimized. More particularly, the purpose of the ERP assay is to distinguish the effect of various cationic lipids and helper lipid components of SPLPs based on their relative effect on binding/uptake or fusion with/destabilization of the endosomal membrane. This assay allows one to determine quantitatively how each component of the SPLP or other lipid-based carrier system effects transfection efficacy, thereby optimizing the SPLPs or other lipid-based carrier systems. As explained herein, the Endosomal Release Parameter or, alternatively, ERP is defined as:

Reporter Gene Expression/Cell

SPLP Uptake/Cell

It will be readily apparent to those of skill in the art that any reporter gene (e.g., luciferase, β-galactosidase, green fluorescent protein, etc.) can be used. In addition, the lipid component (or, alternatively, any component of the SPLP or lipid-based formulation) can be labeled with any detectable label provided the does inhibit or interfere with uptake into the cell. Using the ERP assay of the present invention, one of skill in the art can assess the impact of the various lipid components (e.g., cationic lipid, non-cationic lipid, PEG-lipid derivative, PEG-DAA conjugate, ATTA-lipid derivative, calcium, CPLs, cholesterol, etc.) on cell uptake and transfection efficiencies, thereby optimizing the SPLP or other lipid-based carrier system. By comparing the ERPs for each of the various SPLPs or other lipid-based formulations, one can readily determine the optimized system, e.g., the SPLP or other lipid-based formulation that has the greatest uptake in the cell coupled with the greatest transfection efficiency.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green®; rhodamine and derivatives, such Texas red, tetrarhodimine isothiocynate (TRITC), etc., digoxigenin, biotin, phycoerythrin, AMCA, CyDyes®, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the SNALP, SPLP, or other lipid-based carrier system using methods well known in the art. As indicated above, a wide variety of labels can be used, with the choice of label depending on sensitivity required, ease of conjugation with the SNALP component, stability requirements, and available instrumentation and disposal provisions.

VI. Liposomes Containing Cationic Lipids

In addition to the SNALP formulations described above, the cationic lipids of the present invention (i.e., cationic lipids of Formula I or Formula II) can be used in the preparation of either empty liposomes or liposomes containing one or more bioactive agents.

A. Liposome Preparation

A variety of methods are available for preparing liposomes as described in, e.g., Szoka, et al., *Ann. Rev. Biophys.* Bioeng., 9:467 (1980), U.S. Pat. Nos. 4,186,183, 4,217,344, 4,235,871, 4,261,975, 4,485,054, 4,501,728, 4,774,085, 4,837,028, 4,946,787, WO 91/17424, Deamer and Bangham, *Biochim. Biophys. Acta,* 443:629-634 (1976); Fraley, et al., *PNAS. USA,* 76:3348-3352 (1979); Hope, et al., *Biochim. Biophys. Acta,* 812:55-65 (1985); Mayer, et al., *Biochim. Biophys. Acta,* 858:161-168 (1986); Williams, et al., *Proc. Natl. Acad. Sci.,* 85:242-246 (1988), the text Liposomes, Marc J. Ostro, ed., Marcel Dekker, Inc., New York, 1983, Chapter 1, and Hope, et al., *Chem. Phys. Lip.,* 40:89 (1986). Suitable methods include, but are not limited to, sonication, extrusion, high pressure/homogenization, microfluidization, detergent dialysis, calcium-induced fusion of small liposome vesicles, and ether-infusion methods, all of which are well known in the art.

One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles can be prepared by sonication or extrusion. Sonication is generally performed with a tip sonifier, such as a Branson tip sonifier, in an ice bath. Typically, the suspension is subjected to severe sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass. Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes which have not been sized during formation may be sized to achieve a desired size range and relatively narrow distribution of liposome sizes. A size range of about 0.2-0.4 microns allows the liposome suspension to be sterilized by filtration through a conventional filter. The filter sterilization method can be carried out on a high through-put basis if the liposomes have been sized down to about 0.2-0.4 microns.

Several techniques are available for sizing liposomes to a desired size. One sizing method is described in U.S. Pat. No. 4,737,323. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.,* 10:421-450 (1981). Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred. In particularly preferred embodiments, liposomes are between about 0.05 and about 0.2 microns.

In preferred embodiments, empty liposomes are prepared using conventional methods known to those of skill in the art.

B. Use of Liposomes as Delivery Vehicles

The drug delivery compositions of the present invention (e.g., liposomes, micelles, lipid-nucleic acid particles, virosomes, etc.) are useful for the systemic or local delivery of therapeutic agents or bioactive agents and are also useful in diagnostic assays.

The following discussion refers generally to liposomes; however, it will be readily apparent to those of skill in the art that this same discussion is fully applicable to the other drug delivery systems of the present invention (e.g., micelles, virosomes, lipoplexes, lipid-nucleic acid particles, etc., all of which can be advantageously formed using the cationic lipids of Formula I or II as described herein).

For the delivery of therapeutic or bioactive agents, the cationic lipid-containing liposome compositions can be loaded with a therapeutic agent and administered to the subject requiring treatment. The therapeutic agents which are administered using the compositions and methods of the present invention can be any of a variety of drugs that are selected to be an appropriate treatment for the disease to be treated. Often the drug will be an antineoplastic agent, such as vincristine (as well as the other vinca alkaloids), doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues using the compounds and methods of the present invention. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; antidepressants, e.g., imipramine, amitriptyline and doxepim; anti-conversants, e.g., phenyloin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

As mentioned above, cationic lipids can be used in the delivery of therapeutic genes or oligonucleotides intended to induce or to block production of some protein within the cell. Nucleic acid is negatively charged and may be combined with a positively charged entity to form an SPLP suitable for formulation and cellular delivery of nucleic acid as described above.

Another clinical application of the cationic lipids of this invention is as an adjuvant for immunization of both animals and humans. Protein antigens, such as diphtheria toxoid, cholera toxin, parasitic antigens, viral antigens, immunoglobulins, enzymes and histocompatibility antigens, can be incorporated into or attached onto the liposomes containing the cationic lipids of the present invention for immunization purposes.

Liposomes containing the cationic lipids of the present invention are also particularly useful as carriers for vaccines that will be targeted to the appropriate lymphoid organs to stimulate an immune response.

Liposomes containing the cationic lipids of the present invention can also be used as a vector to deliver immunosuppressive or immunostimulatory agents selectively to cells of interest. For example, glucocorticoids useful to suppress macrophage activity and lymphokines that activate macrophages can be delivered using the liposomes of the present invention.

Liposomes containing the cationic lipids of the present invention and containing targeting molecules can be used to selectively modulate many biological activities. For example, liposomes incorporating a particular antigen can be employed to stimulate the proliferation of B cells displaying surface antibodies that specifically bind the antigen, thus inducing an immune response specific for the antigen. As another example, liposomes incorporating growth factors or lymphokines on their surface can be directed to stimulate cells expressing the appropriate receptors for these factors. Using this approach, proliferation of bone marrow cells can be stimulated as part of a therapeutic regimen (e.g., treatment of cancer).

Liposomes containing the cationic lipids of the present invention can be used to deliver any product (e.g., therapeutic agents including nucleic acids, diagnostic agents, labels or other compounds) to a cell or tissue, including cells and tissues in mammals.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. In one embodiment, the liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposome's surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) I: and Leonetti, et al., *PNAS USA* 87:2448-2451 (1990)). Examples of targeting moieties can also include other proteins, specific to cellular components, including antigens associated with neoplasms or tumors. Proteins used as targeting moieties can be attached to the liposomes via covalent bonds. See, Heath, Covalent Attachment of Proteins to Liposomes, 149 Methods in Enzymology 111-119 (Academic Press, Inc. 1987). Other targeting methods include the biotin-avidin system.

In some cases, the diagnostic targeting of the liposome can subsequently be used to treat the targeted cell or tissue. For example, when a toxin is coupled to a targeted liposome, the toxin can then be effective in destroying the targeted cell, such as a neoplastic cell.

C. Use of the Liposomes as Diagnostic Agents

The drug delivery compositions, e.g., liposomes, prepared using the cationic lipids of the present invention can be labeled with markers that will facilitate diagnostic imaging of various disease states including tumors, inflamed joints, lesions, etc. Typically, these labels will be radioactive markers, although fluorescent labels can also be used. The use of gamma-emitting radioisotopes is particularly advantageous as they can easily be counted in a scintillation well counter, do not require tissue homogenization prior to counting and can be imaged with gamma cameras.

Gamma- or positron-emitting radioisotopes are typically used, such as $^{99}$Tc, $^{24}$Na, $^{51}$Cr, $^{59}$Fe, $^{67}$Ga, $^{86}$Rb, $^{111}$In, $^{125}$I, and $^{195}$Pt as gamma-emitting; and such as $^{68}$Ga, $^{82}$Rb, $^{22}$Na, $^{75}$Br, $^{122}$I and $^{18}$F as positron-emitting. The liposomes can also be labelled with a paramagnetic isotope for purposes of in vivo diagnosis, as through the use of magnetic resonance imaging (MRI) or electron spin resonance (ESR). See, for example, U.S. Pat. No. 4,728,575.

D. Loading the Liposomes

Methods of loading conventional drugs into liposomes include, for example, an encapsulation technique, loading into the bilayer and a transmembrane potential loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. Nos. 4,885,172, 5,059,421, and 5,171,578. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., Na$^+$, K$^+$ and/or H$^+$) across the membranes. This concentration gradient is generated by producing liposomes having different internal and external media and has an associated proton gradient. Drug accumulation can than occur in a manner predicted by the Henderson-Hasselbach equation.

The liposome compositions of the present invention can by administered to a subject according to standard techniques. Preferably, pharmaceutical compositions of the liposome compositions are administered parenterally, i.e., intraperitoneally, intravenously, subcutaneously or intramuscularly. More preferably, the pharmaceutical compositions are administered intravenously by a bolus injection. Suitable formulations for use in the present invention are found in Remington's Pharmaceutical Sciences, Mack Publishing Company, Philadelphia, Pa., 17th ed. (1985). The pharmaceutical compositions can be used, for example, to diagnose a variety of conditions, or treat a variety of disease states (such as inflammation, infection (both viral and bacterial infectons), neoplasis, cancer, etc.).

Preferably, the pharmaceutical compositions are administered intravenously. Thus, this invention provides compositions for intravenous administration which comprise a solution of the liposomes suspended in an acceptable carrier, preferably an aqueous carrier. A variety of aqueous carriers can be used, e.g., water, buffered water, 0.9% isotonic saline, and the like. These compositions can be sterilized by conventional, well known sterilization techniques, or may be sterile filtered. The resulting aqueous solutions may be packaged for use as is or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of liposome compositions in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgement of the clinician, but will generally be between about 1 and about 5 mg per kilogram of body weight.

EXAMPLES

The invention will be described in greater detail by way of the following examples. The following examples are offered for illustrative purposes, and are not intended to limit the invention in any manner. Those of skill in the art will readily recognize a variety of noncritical parameters which can be changed or modified to yield essentially the same results.

Example 1

Materials and Methods

Materials: DPPS, 1,2-Distearoyl-sn-glycero-3-phosphocholine (DSPC) and cholesterol were purchased from Avanti Polar Lipids (Alabaster, Ala.). TNS was obtained from Sigma-Aldrich Canada (Oakville, ON). RiboGreen was obtained from Molecular Probes (Eugene, Oreg.). The alkyl mesylates were purchased from Nu-Chek Prep, Inc. (Elysian, Minn., USA). siRNA (anti-luciferase and mismatch control) was purchased from Dharmacon (Lafayette, Colo., USA). The anti-luciferase sense sequence was 5'-GAUUAUGUC-CGGUUAUGUAUU-3' (SEQ ID NO:1). The anti-luciferase antisense sequence was 5'-UACAUAACCGGACAUAAU-CUU-3' (SEQ ID NO:2). All other chemicals were purchased from Sigma-Aldrich (Oakville, ON, Canada).

Synthesis of DSDMA and DODMA: DSDMA and DODMA were synthesized using the respective alkyl bromides with methodology derived from that of a DOTMA precursor (Felgner et al, PNAS USA, 84, 7413-7417 (1987)). 3-(Dimethylamino)-1,2-propanediol (714 mg, 6 mmol) and 95% sodium hydride (NaH, 1.26 g, 50 mmol) were stirred in benzene (30 mL) under argon for 30 minutes. The correct (either oleyl or stearyl) alkyl bromide (5.0 g, 15 mmol) was added and the reaction refluxed under argon for 18 hours. The reaction mixture was then cooled in an ice bath while quenching via the slow addition of ethanol. Following dilution with a further 150 mL of benzene, the mixture was washed with distilled water (2×150 mL) and brine (150 mL), using ethanol (~20 mL) to aid phase separation if necessary. The organic phase was dried over magnesium sulphate and evaporated. The crude product was purified on a silica gel (Kiesel Gel 60) column eluted with chloroform containing 0-5% methanol. Column fractions were analyzed by thin layer chromatography (TLC) (silica gel, chloroform/methanol 9:1 v/v, visualized with molybdate) and fractions containing pure product ($R_f$=0.5) were pooled and concentrated. The product was decolorized by stirring for 30 minutes in a suspension of activated charcoal (1 g) in ethanol (75 mL) at 60° C. The charcoal was removed by filtration through Celite, and the ethanol solution concentrated to typically yield 2.4 g (65%) of pure product. $^1$H-NMR (DSDMA): $\delta_H$ 3.65-3.32 (m, 7H, OCH, 3×OCH$_2$), 2.45-2.31 (m, 2H, NCH$_2$), 2.27 (s, 6H, 2×NCH$_3$), 1.61-1.45 (m, 4H, OCH$_2$C$\underline{H_2}$), 1.40-1.17 (m, 60H, H$_{stearyl}$), 0.86 (t, 6H, CH$_2$C$\underline{H_3}$). $^1$H-NMR (DODMA): $\delta_H$ 5.4-5.27 (m, 4H, 2×C$\underline{H}$=C$\underline{H}$), 3.65-3.35 (m, 7H, OCH, 3×OCH$_2$), 2.47-2.33 (m, 2H, NCH$_2$), 2.28 (s, 6H, 2×NCH$_3$), 2.06-1.94 (m, 8H, 4×C$\underline{H_2}$CH=CH), 1.61-1.50 (m, 4H, OCH$_2$C$\underline{H_2}$), 1.38-1.20 (m, 48H, H$_{oleyl}$), 0.88 (t, 6H, CH$_2$C$\underline{H_3}$).

Synthesis of DLinDMA and DLenDMA: The DLinDMA and DLenDMA were synthesized similarly to the DSDMA and DODMA, but used the alkyl mesylates instead of alkyl bromides. The general synthetic protocol was identical for those of DSDMA and DODMA, substituting the alkyl mesylates for the bromides in the same molar ratios. The activated charcoal decolorization step was omitted, since the products here contain conjugated double bonds and activated charcoal is expected to adsorb compounds containing such features. Yields were typically 2.0 g (55%). $^1$H-NMR (DLinDMA): $\delta_H$ 5.43-5.27 (m, 8H, 4×C$\underline{H}$=C$\underline{H}$), 3.65-3.35 (m, 7H, OCH, 3×OCH$_2$), 2.77 (t, 4H, =CHC$\underline{H_2}$CH=), 2.47-2.33 (m, 2H, NCH$_2$), 2.28 (s, 6H, 2×NCH$_3$), 2.05 (q, 8H, 4×CH$_2$C$\underline{H_2}$CH=), 1.62-1.50 (m, 4H, OCH$_2$CH$_2$), 1.40-1.22 (m, 32H, $\overline{H}_{linoleyl}$), 0.89 (t, 6H, CH$_2$CH$_3$). $^1$H-NMR (DLenDMA): $\delta_H$ 5.44-5.27 (m, 8H, 4×C$\underline{H}$=C$\underline{H}$), 3.62-3.48 (m, 7H, OCH, 3×OCH$_2$), 2.80 (t, 4H, =CHC$\underline{H}^2$CH=), 2.43-2.32 (m, 2H, NCH$_2$), 2.26 (s, 6H, 2×NCH$_3$), 2.12-1.99 (m, 8H, 4×CH$_{2/3}$C$\underline{H_2}$CH=), 1.61-1.51 (m, 4H, OCH$_2$C$\underline{H}^2$), 1.40-1.22 (m, 20H, $\overline{H}_{linolenyl}$) 0.98 (t, 6H, CH$_2$CH$_3$).

Synthesis of PEG$_{2000}$-C-DMA: PEG-C-DMA was synthesized as follows. In brief, a C$_{14}$ lipid anchor was prepared by first alkylating the hydroxyl groups of 3-allyloxypropane-1,2-diol with myristyl bromide. The allyl group was subsequently removed via palladium catalysis, resulting in the C$_{14}$ hydroxyl lipid. The hydroxyl group was converted to the primary amine by mesylation and amination to yield 1,2-dimyristyloxypropyl-3-amine, the lipid anchor. Conjugation with PEG was effected by treating monomethoxy poly(ethylene glycol) (average molecular weight 2000) with an excess of diphosgene to form the chloroformate. Addition of the C$_{14}$ amine lipid anchor and stirring overnight yielded PEG$_{2000}$-C-DMA, referred to here as PEG-C-DMA.

SNALP Preparation: SNALP with a lipid composition of DSPC:Chol:PEG-C-DMA:Cationic Lipid (20:48:2:30 molar percent) were prepared using the spontaneous vesicle formation by ethanol dilution method [Jeffs et al., *Pharm. Res*. In Press (2005)]. The sample's were diafiltered against 100 mL of PBS (20 wash volumes) using a cross flow ultrafiltration cartridge (Amersham Biosciences, Piscataway, N.J.) and sterile filtered through Acrodisc 0.2 μm Posidyne filters (Pall Corp., Ann Arbor, Mich.). The siRNA concentration of final samples was determined using the RiboGreen assay and a siRNA standard curve. Particle size and polydispersity was determined using a Malvern Instruments Zetasizer 3000HSA (Malvern, UK). Nucleic acid encapsulation was determined using a RiboGreen assay, comparing fluorescence in the presence and absence of Triton X-100. RiboGreen fluorescence was measured using a Varian Eclipse Spectrofluorometer (Varian Inc) with $\lambda_{ex}$=500 nm, $\lambda_{em}$=525 nm.

TNS Assay: 20 μM of SNALP lipid and 6 μM of TNS were mixed in a fluorescence cuvette in 2 mL of 20 mM sodium phosphate, 25 mM citrate, 20 mM ammonium acetate and 150 mM NaCl, at a pH that was varied from 4.5 to 9.5. Fluorescence was determined at each pH using a Varian Eclipse Spectrofluorometer (Varian Inc) with settings of $\lambda_{ex}$=322 nm, $\lambda_{em}$=431 nm. Fluorescence for each system at the various pH was then normalized to the value at pH 4.5. The pK$_a$ values are the point at which 50% of the molecules present are charged. By assuming that minimum fluorescence represents zero charge, and maximum fluorescence represents 100% charge, pK$_a$ can be estimated by measuring the pH at the point exactly half way between the values of minimum and maximum charge.

$^{31}$P Nuclear Magnetic Resonance Spectroscopy: Multilamellar vesicles (MLV) were prepared comprising DPPS and cationic lipid at a molar ratio of 1:1. This was accomplished by drying the lipids from chloroform solution, transferring to 10 mm NMR tubes, and hydrating in 1.5 mL of 10 mM sodium citrate, pH 4. Free induction decays (FIDs) corresponding to 1000 scans were obtained with a 3.0 μs, 60o pulse with a 1 s interpulse delay and a spectral width of 25000 Hz. A gated two-level proton decoupling was used to ensure sufficient decoupling with minimum sample heating. An exponential multiplication corresponding to 50 Hz of line broadening was applied to the FIDs prior to Fourier transformation. The sample temperature (+/−1° C.) was regulated using a Bruker B-VT1000 variable temperature unit. Chemical shifts were referenced to 85% phosphoric acid as an external standard.

In vitro Transfection: Cells were cultured in MEM (Invitrogen) containing 10% fetal bovine serum (FBS) (CanSera) and 0.25 mg/mL G418 (Invitrogen). Neuro2A-G cells (Neuro2A cells stably transfected to express luciferase [R. E. Kingston. in *Current Protocols in Molecular Biology, Vol.* 2, pp. 9.1.4-9.1.9, John Wiley & Sons, Inc. (1997)]) were plated at a concentration of 4×10$^4$ cells per well in 24-well plates and grown overnight. Cells were treated with SNALP at doses of 0.0625-1.0 μg/mL nucleic acid (AntiLuc Active or Mismatch Control) and incubated for 48 hours at 37° C. and 5% CO$_2$. Cells were then washed with PBS and lysed with 200 μL 250 mM sodium phosphate containing 0.1% Triton X-100. The luciferase activity for each well was determined using Luciferase Reagent (Promega) and a standard luciferase protein (Roche). The luminescence for each was measured using a Berthold MicroLumatPlus LB96V plate luminometer. The resulting luciferase activity was then normalized for the amount of protein using the Micro BCA assay kit (Pierce). Luciferase knockdown relative to a control was then determined for each system.

Cellular Uptake: SNALP were prepared incorporating the non-exchangeable tritium-labeled lipid cholesteryl hexadecyl ether (3H—CHE) (11.1 μCi/μmol total lipid) [Bally et al., in *Liposome Technology*, Vol. III, pp. 27-41, CRC Press (1993)]. Neuro2A cells (ATCC, VA, USA) were plated in 12 well plates at 1.6×105 cells per well in minimal essential media. The following day, media was removed and replaced with media containing radiolabelled SNALP at 0.5 μg/mL nucleic acid. After 24 hours, the media and unincorporated SNALP were removed, adherent cells gently washed 4 times with PBS, and then lysed with 600 μL Lysis Buffer (250 mM phosphate with 0.1% Triton X-100). The resulting cell lysate (500 μL) was added to glass scintillation vials containing 5 mL Picofluor 40 (Perkin Elmer) and $^3$H—CHE was determined using a Beckman LS6500 scintillation counter (Beckman Instruments). The protein content of cell lysates was determined using the Micro BCA assay (Pierce). Uptake was expressed as a percentage of the total amount of activity applied to the cells per mg of cellular protein.

Uptake of SNALP Containing Cy3-labeled siRNA: SNALP were formulated as previously described, but using siRNA labelled with the fluorophore Cy3 (Cy3-siRNA was a gift of Sirna Therapeutics Inc, Boulder, Colo.). The encapsulation, siRNA concentration, and particle size were determined as described.

For the uptake study, $8 \times 10^4$ Neuro2A-G cells were grown overnight on 4-well chamber slides (BD Falcon, Mississauga, ON) in MEM containing 0.25 mg/mL G418. DSDMA, DODMA, DLinDMA, and DLenDMA SNALP containing Cy3-siRNA, as well as naked Cy3-siRNA and unlabeled DSDMA SNALP were placed on the cells at 0.5 µg/mL siRNA. After a 4 hour incubation with the transfection media, the cells were washed with PBS, then with MEM containing G418 and finally with PBS once more. The cells were then fixed in a 4% paraformaldehyde solution in PBS for 10 min at room temperature. The cells were washed with PBS and stained with 300 nM DAPI (Molecular Probes, Eugene, Oreg.) in PBS for 5 minutes. The cells were washed with PBS, the mounting media ProLong Gold Antifade Reagent (Molecular Probes, Eugene, Oreg.) applied and a cover slip added. The cells were viewed using an Olympus BX60 Microscope modified for fluorescence capabilities. Cy3 fluorescence within the cells was visualized using a rhodamine cube set (Microgen Optics, Redding, Calif.) and the DAPI fluorescence was visualized using a DAPI cube set (Carsen Group, Markham, ON). Digital pictures were captured using an Olympus DP70 camera system. Pictures of the cells were taken at exposure times of ¼ sec when examining Cy3 fluorescence and 1/80 sec when examining DAPI fluorescence.

Example 2

Assays for Serum Stability

Lipid/nucleic acid particles formulated according to the above noted techniques can be assayed for serum stability by a variety of methods.

For instance, in a typical DNase 1 digestion, 1 µg of DNA encapsulated in the particle of interest is incubated in a total volume of 100 µL of 5 mM HEPES, 150 mM NaCl, 10.0 mM $MgCl_2$ pH 7.4. DNase treated samples are treated with either 100 or 10 U of DNase I (Gibco-BRL). 1.0% Triton X-100 can be added in control experiments to ensure that lipid formulations are not directly inactivating the enzyme. Samples are incubated at 37° C. for 30 min after which time the DNA is isolated by addition of 500 µL of DNAZOL followed by 1.0 mL of ethanol. The samples are centrifuged for 30 min at 15,000 rpm in a tabletop microfuge. The supernatant is decanted and the resulting DNA pellet is washed twice with 80% ethanol and dried. This DNA is resuspended in 30 µL of TE buffer. 20 µL of this sample is loaded on a 1.0% agarose gel and subjected to electrophoresis in TAE buffer.

In a typical serum assay, 50 µg of DNA in free, encapsulated, or encapsulated+0.5% Triton X100 was aliquoted into 1.5 mL Eppendorf tubes. To the tubes were added 45 µl normal murine or human serum, dH2O (to make final volume 50 µL). The tubes were sealed with parafilm and incubated at 37° C. A sample of the free, encapsulated, or encapsulated+ 0.5% Triton X100 not digested by nuclease (standard) was frozen in liquid nitrogen in an Eppendorf tube and stored at −20° C. Aliquots were taken at various time points, added to GDP buffer containing proteinase K (133 µg/mL) and immediately frozen in liquid nitrogen to stop the reaction. Once all of the time points were collected, the samples were incubated at 55° C. in a waterbath to activate proteinase K enabling it to denature any remaining exonuclease. Proteinase K digested samples were applied to polyacrylamide gels to assess levels of exonuclease degradation.

Particles disclosed above demonstrate serum stability by showing less than 5% and preferably undetectable amounts of DNA degradation (partial or total) as a result of such treatment, even in the presence of 100 U DNase 1. This compares favorably to free DNA, which is completely degraded, and plasmid/lipid complexes (such as DOTMA or DODAC: DOPE complexes), wherein DNA is substantially (i.e., greater than 20%, often 80%) degraded after such treatment.

Example 3

Synthesis of
1,2-DiLinoleyloxy-N,N-dimethylaminopropane
(DLinDMA) and
1,2-Dilinolenyloxy-N,N-dimethylaminopropane
(DLenDMA)

3-(Dimethylamino)-1,2-propanediol (714 mg, 6 mmol) and 95% sodium hydride (NaH, 1.26 g, 50 mmol) are stirred in benzene (30 mL) under nitrogen for 30 minutes. Linoleyl mesylate (5.0 g, 15 mmol) is added and the reaction refluxed under nitrogen for 3 hours. The reaction mixture is then cooled in an ice bath while quenching via the slow addition of ethanol. Following dilution with a further 150 mL of benzene, the mixture is washed with distilled water ($2 \times 150$ mL) and brine (150 mL). The organic phase is dried over magnesium sulphate and evaporated to give the crude product. The crude product is purified on a silica gel (Kiesel Gel 60) column eluted with 0-5% methanol in chloroform. Column fractions are analyzed by thin layer chromatography (TLC) (silica gel, chloroform/methanol 9:1 v/v, visualized with molybdate dip) and fractions containing purified product ($R_f$=0.5) are pooled and concentrated.

Decolorization and further purification of DLinDMA is effected with a second column, this time eluting with 20-50% ethyl acetate in hexane. Column fractions are analyzed by TLC (silica gel, ethyl acetate/hexane 1:1 v/v, visualized with molybdate) and fractions containing pure product ($R_f$=0.4) are pooled and concentrated. The procedure described herein typically yields 2.2 g (60%) of pure product.

For synthesis of DLenDMA, linolenyl mesylate is substituted for linoleyl mesylate and the remainder of the synthesis, decolorization, and purification reactions is carried out as described above.

Example 4

Formulation Characteristics of Unsaturated Lipids Are Uniform and Reproducible

This example sets forth the physical properties of the SNALP formulations described herein. SNALP containing the various cationic lipids were prepared as described and encapsulated RNA and particle size assessed (Table 1 below). The three unsaturated cationic lipids resulted in formulations that were approximately the same size (132-140 nm). Polydispersity of all formulations was low, indicating a narrow distribution of particle size. RNA encapsulation in the final particles was 84-85% of the total. Attempts to encapsulate siRNA in SNALP using the saturated lipid DSDMA resulted in the formation of slightly larger particles (180 nm) with encapsulation of 67%.

Percentage Encapsulation was determined using the RiboGreen fluorescence assay to measure the amount of encapsulated nucleic acid relative to the total nucleic acid present. Particle diameter and polydispersity was measured using a Malvern Zetasizer. Values are the mean of 3 separate experiments, the error is standard deviation.

| Cationic Lipid | % Encapsulation | Diameter (nm) | Polydispersity |
|---|---|---|---|
| DSDMA | 67 ± 3 | 182 ± 11 | 0.15 ± 0.03 |
| DODMA | 84 ± 1 | 137 ± 4 | 0.12 ± 0.01 |
| DLinDMA | 84 ± 3 | 140 ± 6 | 0.11 ± 0.02 |
| DLenDMA | 85 ± 1 | 132 ± 7 | 0.13 ± 0.03 |

Example 5 pKa of Cationic Lipids is Influenced by Saturation

Figure 5:
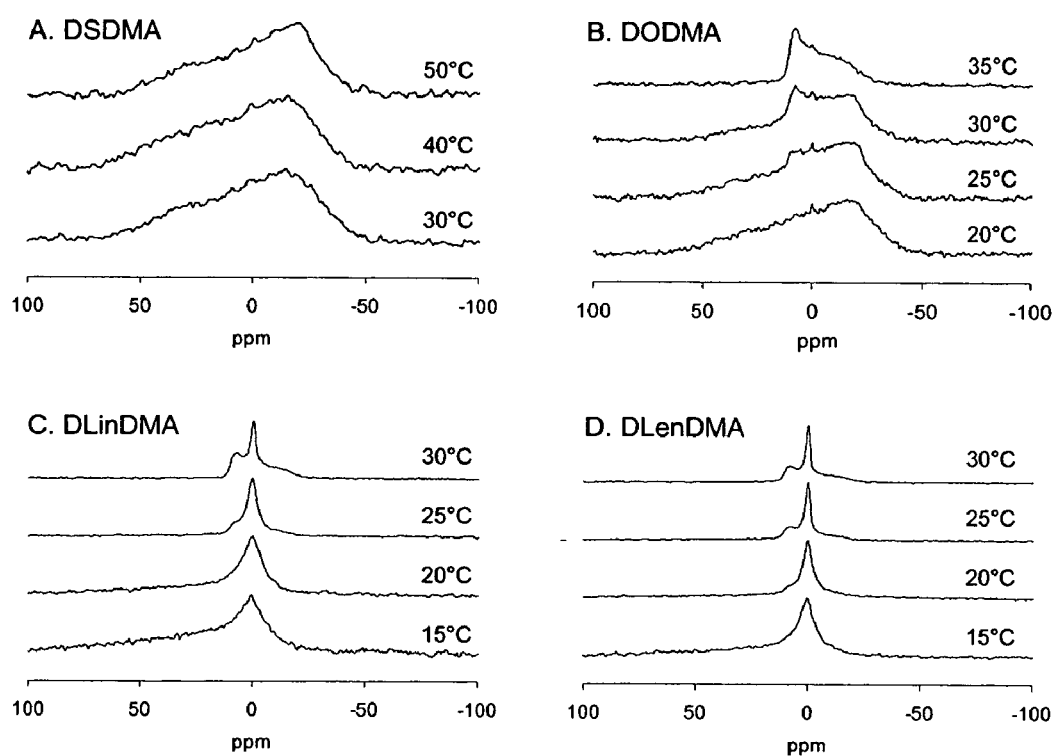
FIG. 5 illustrates data showing the results of $^{31}$P-NMR analysis to determine the effect of unsaturation on phase transition temperature.

The apparent $pK_a$ of the cationic lipids was determined as described in Example 1 above. Our determination of lipid $pK_a$ utilized 2-(p-toluidino)naphthalene-6-sulfonic acid, a negatively charged indicator of membrane potential (Bailey and Cullis, *Biochemistry* 33 12573-80 (1994)). TNS is electrostatically attracted to positively charged membranes. Subsequent adsorption to the lipid membrane results in the immediate environment of the TNS becoming more lipophilic, removing the water molecules that otherwise quench TNS fluorescence. Since TNS is more readily absorbed by positively charged membranes, TNS fluorescence is an indicator of positive membrane surface charge. The surface $pK_a$ values of each SNALP formulation were determined by varying the local pH in the presence of TNS. In FIG. 5, it can be seen that formulations containing unsaturated lipids have similar $pK_a$ values (6.7-7.0) suggesting that the particles are charge neutral at physiological pH but become positively charged at endosomal pH. The saturated lipid DSDMA, however, generated particles with a higher $pK_a$ of approximately 7.6. SNALP particles containing DSDMA would be expected to be charged at physiological pH.

The results shown in FIG. 5 demonstrate that lipid $pK_a$ correlated with degree of saturation with DSDMA, DODMA, DLinDMA, and DLenDMA exhibiting $pK_a$s of 7.6, 7.0, 6.7, and 6.7, respectively.

Example 6

The Bilayer-to-Hexagonal Phase Transition Temperature Increases with Alkyl Chain Saturation The significance of saturation with respect to phase transition temperature was investigated using $^{31}$P-NMR. Lipid polymorphism in anionic phospholipid/cationic lipid mixtures has been examined by others using this technique, facilitated by the presence of a phosphate group in the phospholipid (Epand et al., *Chem. Phys. Lipids* 57 75-80 (1991)); Felgner et al., *PNAS USA* 84 7413-7417 (1987)). The shape of the NMR trace varies depending on the arrangement of the lipids. A bi-layer structure yields a high field peak with a low field shoulder. However, above the Phase Transition Temperature, ($T_c$), lipids adopt a fusogenic $H_{II}$ phase, indicated by a reversed pattern with the peak appearing on the low field side. $^{31}$P-NMR studies have previously shown that above certain temperatures (the Phase Transition Temperature, $T_c$), lipids may adopt the fusogenic $H_{II}$ phase [Epand et al., *Chem. Phys. Lipids* 57 75-80 (1991); Felgner et al., *PNAS USA* 84 7413-7417 (1987)]. A higher temperature required to convert a bilayer (Lα phase) to the $H_{II}$ phase indicates a less fusogenic bilayer. By determining the temperature at which the conversion occurs, the relative ease with which the lipids form the $H_{II}$ phase, their 'fusogenicity', can be determined.

MLV were prepared using the anionic lipid DPPS in a 1:1 molar ratio with each cationic lipid. The $^{31}$P-NMR spectra of the MLV were measured at various temperatures. MLV containing the saturated lipid DSDMA showed no appreciable sign of adopting the $H_{II}$ phase, even at temperatures as high as 50° C. However DODMA (1 double bond per alkyl chain) containing MLV exhibit a phase transition temperature between 30 and 35° C. The presence of a second double bond (DLinDMA) reduced the $T_c$ still further to between 20 and 25° C., while incorporation of a 3rd double bond (DLenDMA) has little further effect. As can be seen in FIG. 6A, for the DSDMA/DPPS system, the bilayer pattern occurs from temperatures of 30 to 50° C. (a high-field peak with a low-field shoulder). Therefore, DSDMA would appear to have very little ability to form $H_{II}$ phases in conjunction with the anionic lipid. The cationic lipid with a single double bond, DODMA, possesses a transition temperature between 30 and 35° C. (FIG. 6B). The DLinDMA (2 double bonds) and DLenDMA (3 double bonds) systems exhibit somewhat similar transition temperatures between 20 and 25° C. (FIGS. 6C and 6D). It should be noted that the central, isotropic peak seen in traces 6C and 6D does not represent the phase transition temperature but rather results from small phospholipid vesicles that are also present in the preparation. The shift in lineshape asymmetry from a high-field peak/low-field shoulder (bi-layer phase, lower temperatures) to low-field peak/high-field shoulder (inverted hexagonal phase, higher temperatures) is an indication of phase transition. This is exhibited, inter alia, in trace 6B (DODMA). Based on these results we postulated that the fusogenicity of SNALPs comprising the cationic lipids would increase in the following order: DSDMA<<DODMA<DLinDMA≈DLenDMA and hypothesized that the potency of the SNALPs with respect to nucleic acid delivery would demonstrate a similar hierarchy (DSDMA<<DODMA<DLinDMA≈DLenDMA).

Example 7

Silencing of Gene Expression Following Delivery of siRNA Encapsulated in SPLP Comprising Cationic Lipids This example describes experiments comparing expression of nucleic acids following in vitro transfection of Neuro2A cells with SNALP comprising: (1) DODAC, DODMA, or DLinDMA; (2) PEG-C-DMA; and (3) an siRNA duplex directed against luciferase encapsulated in the SNALP (i.e., siRNA comprising the following sequence: GAUUAUGUCCGGUUAUGUAUU (SEQ ID NO:1) and targeting the DNA sequence complementary to: GATTATGTCCGGTTATGTATT (SEQ ID NO:3)). Neuro2A cells were stably transfected with a plasmid encoding luciferase under the control of the CMV promoter (pLO55). The stably transfected cells were then transfected with SNALP comprising: 15, 20, 25, 30, 35, or 40% of DODAC, DODMA, or DLinDMA; 2% PEG-C-DMA, and an siRNA duplex directed against luciferase encapsulated in the SNALP. Luciferase protein expression was measured 48 hours after transfection with SNALP. SNALP comprising 30% DLinDMA was more effective in reducing luciferase expression in the Neuro2A cells than SNALP comprising DODAC or DODMA were. These results are shown in FIG. 6.

Figure 6:
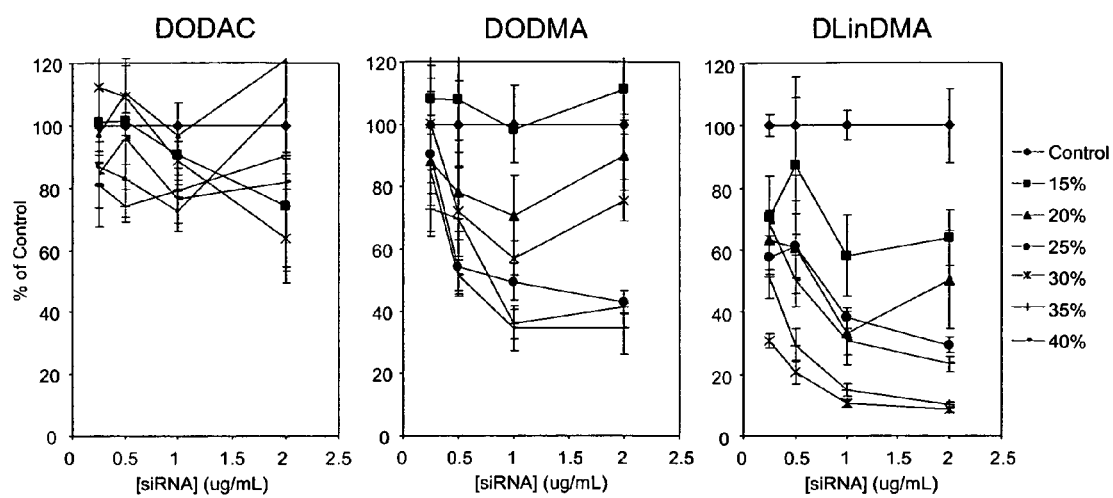
FIG. 6 illustrates data showing silencing of gene expression following in vitro transfection of Neuro2a cells stably expressing luciferase by an SPLP (i.e., SNALP) comprising DODAC, DODMA, or DLinDMA and encapsulating an anti-luciferase siRNA sequence.

As shown in FIG. 6, the results of luciferase gene silencing experiments, using SNALP to deliver siRNA directed against the luciferase gene supported the $^{31}$P-NMR data. Cells were treated with SNALP containing each of the four cationic lipids (i.e., DSDMA, DODMA, DLinDMA, and DLenDMA). After 48 hours, SNALP containing DSDMA, which was shown to be poorly fusogenic by NMR, had no effect on luciferase gene expression. In contrast, the unsaturated lipid formulations, which are more amenable to $H_{II}$ phase formation, resulted in significant silencing of the luciferase gene. Further, the extent of silencing corresponds with the propensity for each cationic lipid to form the fusogenic $H_{II}$ phase. DLinDMA, the most fusogenic lipid with the lowest apparent phase transition temperature, yielded the greatest knockdown when incorporated in SNALP, with luciferase expression only 21% that of the untreated control. This was followed by the DLenDMA formulation (32%), and DODMA (54%). The close correspondence between knockdown efficiency and the $H_{II}$ phase forming ability of the cationic lipid as observed suggests that the two parameters are linked.

Example 8

SNALP Containing Unsaturated Cationic Lipids Show Increased Gene-Silencing Activity The ability of SNALP containing each of the four cationic lipids (i.e., DSDMA, DODMA, DLinDMA, and DLenDMA) to effect gene silencing in stably transfected Neuro2A cells was evaluated. Neuro2A cells stably transfected to express the luciferase were treated with SNALP containing anti-luciferase siRNA for 48 hours. Gene-silencing efficiency was evaluated by comparing the remaining luciferase activity in these cells to that remaining in cells treated with control SNALP containing mismatch siRNA.

Figure 7:
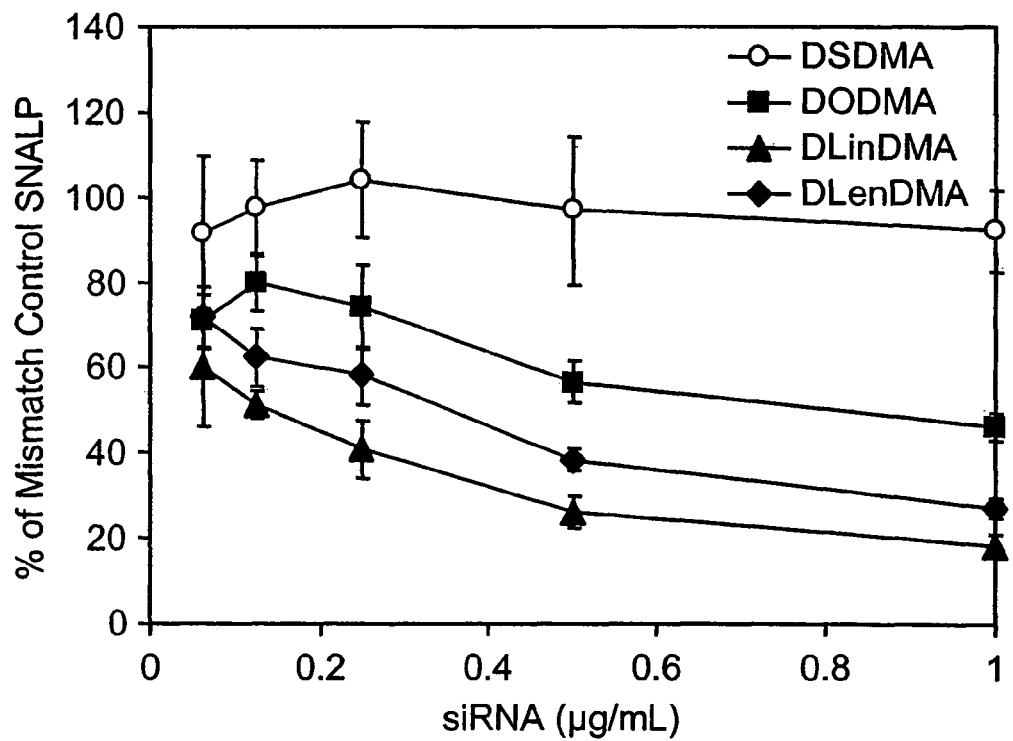
FIG. 7 illustrates data showing SNALP-mediated gene silencing in vitro.

It was found that, as hypothesized, knockdown efficiency corresponded to the ability of lipids to form the fusogenic inverted hexagonal phase. Formulations comprising the saturated lipid DSDMA demonstrated no activity. As unsaturation in the lipid's alkyl chain increased, so did the capacity for RNA interference, with DLinDMA particles yielding an 80% knockdown in gene expression. $^{31}$P-NMR established DLinDMA as having the lowest phase transition temperature in the series and accordingly, being the most fusogenic lipid. Particles comprising DLenDMA, the most unsaturated lipid, were slightly less efficient than those containing DLinDMA. All results were found to be significant by t-Test (P<0.05 at siRNA concentration of 0.5 μg/mL, and P<0.01 at siRNA concentration of 1.0 μg/mL). Error bars represent standard deviation, n=3. The results are shown in FIG. 7.

Example 9

In Vivo Transfection of Organs by Various SPLP Formulations

This example describes experiments demonstrating in vivo transfection of organs with that SPLP comprising 15% DLinDMA can be used SPLP encapsulating a plasmid encoding luciferase under the control of the CMV promoter were administered to Neuro2A tumor bearing male A/J mice. The SPLP had the following formulations:

| | Sample Description |
|---|---|
| A | SPLP-PEG$_{2000}$-C-DMA (CHOL:DSPC:DODMA:PEG$_{2000}$-C-DMA 55:20:15:10 mol %) |
| B | SPLP-PEG$_{2000}$ DlinDMA (CHOL:DSPC:DlinDMA:PEG$_{2000}$-C-DMA 55:20:15:10 mol %) |
| C | SPLP-PEG$_{750}$-C-DMA/DODMA (CHOL:DSPC:DODMA:PEG$_{750}$-C-DMA 55:20:15:10 mol %) |
| D | SPLP-PEG$_{750}$-C-DMA/DLinDMA (CHOL:DSPC:DlinDMA:PEG$_{750}$-C-DMA 55:20:15:10 mol %) 0.41 mg/ml |
| E | SPLP-High PEG$_{750}$-C-DMA (CHOL:DSPC:DODMA:PEG$_{750}$-C-DMA 50:20:15:15 mol %) |
| F | SPLP-High PEG$_{750}$-C-DMA (CHOL:DSPC:DlinDMA:PEG$_{750}$-C-DMA 50:20:15:15 mol %) |
| G | SPLP-DODAC (CHOL:DSPC:DODMA:PEG$_{2000}$-C-DMA:DODAC 45:20:15:10:10 mol %) 0.35 mg/ml |

Figure 8:
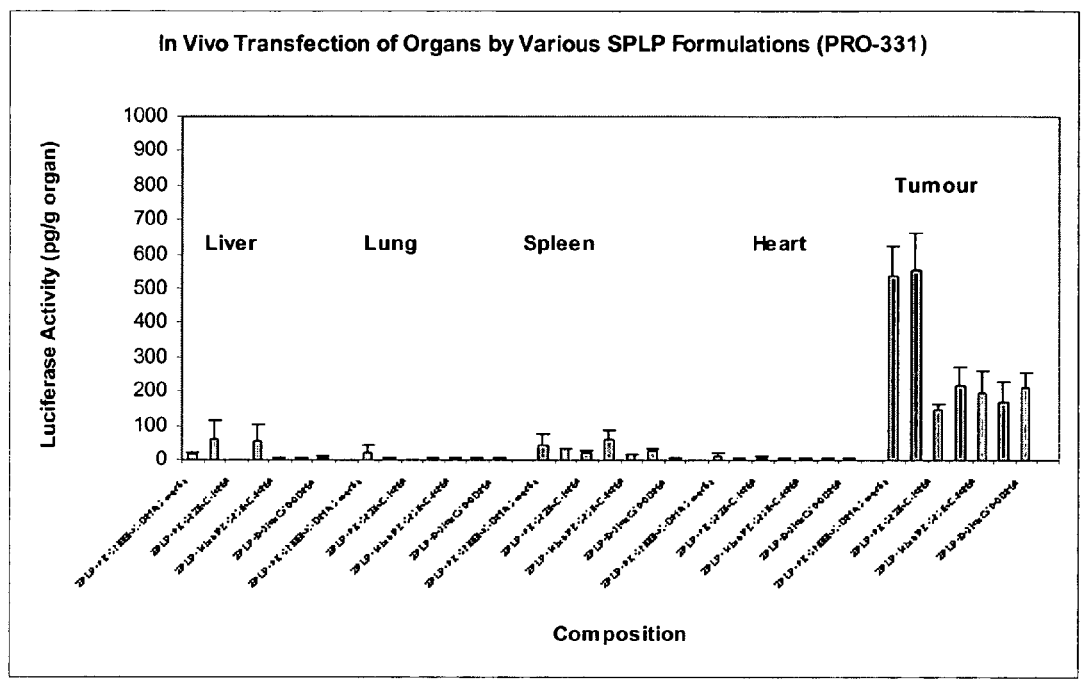
FIG. 8 illustrates data showing luciferase gene expression in tumors 48 hours following intravenous delivery of SPLP encapsulating a plasmid encoding luciferase. The SPLP comprised PEG-C-DMA conjugates and either DODMA or DLinDMA. The PEG moieties had molecular weight of either 2000 or 750.

Luciferase gene expression was assessed in liver, lung, spleen, heart and tumors 48 hours after intravenous administration of the SPLP. The results are shown in FIG. 8.

Example 10

In Vivo Transfection of Tumor by Additional SPLP Formulations

This example describes experiments demonstrating in vivo transfection of organs with that SPLP comprising DLinDMA or DODMA and varying percentages (15%, 10%, 5%, or 2.5%) of PEG-C-DMA. SPLP encapsulating a plasmid encoding luciferase were administered to Neuro2A tumor bearing male A/J mice. The SPLP had the following formulations:

| | Mol % (DSPC:Chol:PEG-C-DMA:DXDMA |
|---|---|
| A | 20:50:15:15 (DODMA) |
| B | 20:55:10:15 (DODMA) |
| C | 20:60:5:15 (DODMA) |
| D | 20:62.5:2.5:15 (DODMA) |
| E | 20:55:10:15 (DLinDMA) |
| F | 20:60:5:15 (DLinDMA) |
| G | 20:62.5:2.5:15 (DLinDMA) |

Figure 9:
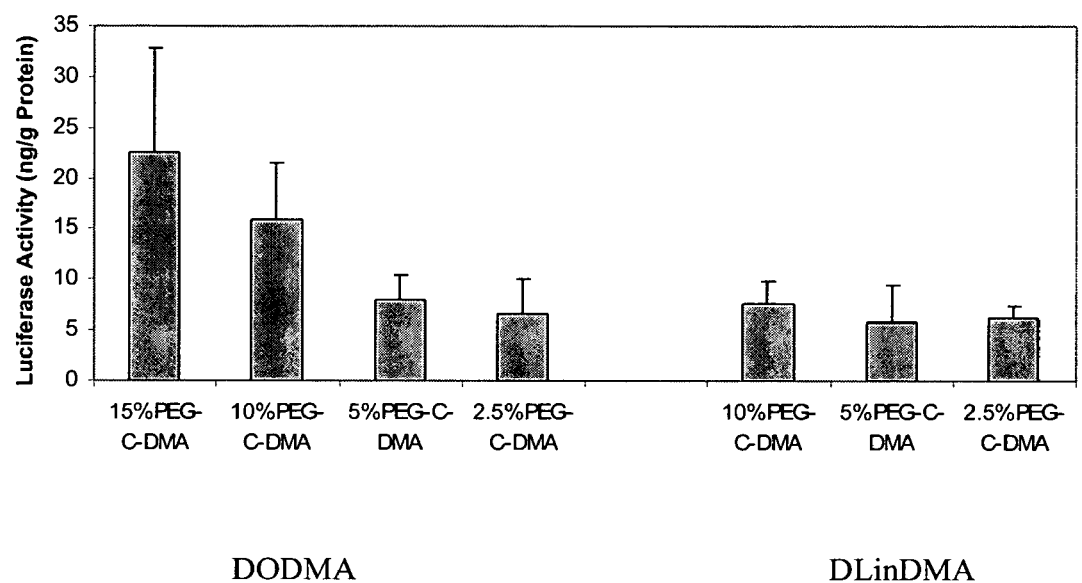
FIG. 9 illustrates data showing luciferase gene expression in Neuro2A tumor bearing male A/J mice 48 hours after intravenous administration of SPLP encapsulating a plasmid encoding luciferase. The SPLP comprised varying percentages (i.e., 15%, 10%, 5% or 2.5%) of PEG-C-DMA and either DODMA or DLinDMA.

Luciferase gene expression was assessed in tumors 48 hours after intravenous administration of SPLP. The results are shown in FIG. 9.

Example 11

Blood Clearance of Lipid Vesicles Comprising PEG-C-DMA

This example describes experiments conducted to assess the blood clearance rate of lipid vesicles comprising various percentages of PEG-C-DMA. A single intravenous dose of $^3$H—CHE-labeled SPLP, SNALP, or empty vesicles was administered to male A/J mice. SPLP comprised the cationic lipid DODMA and SNALP comprised the cationic lipid DLinDMA. The lipid vesicles had the following formulations:

| Group | Treatment | Mol % (DSPC:Chol: PEG-C-DMA:Cationic Lipid) |
|---|---|---|
| A | Empty vesicles | 20:48:2:30 |
| B | SNALP (DlinDMA, PEG-C-DMA) | 20:48:2:30 |
| C | SNALP (DlinDMA, PEG-C-DMA) | 20:55:5:20 |
| D | SPLP (15 mol % PEG-C-DMA) | 20:50:15:15 |
| E | SPLP (10 mol % PEG-C-DMA) | 20:55:10:15 |
| F | SPLP (5 mol % PEG-C-DMA) | 20:60:5:15 |

Figure 10:
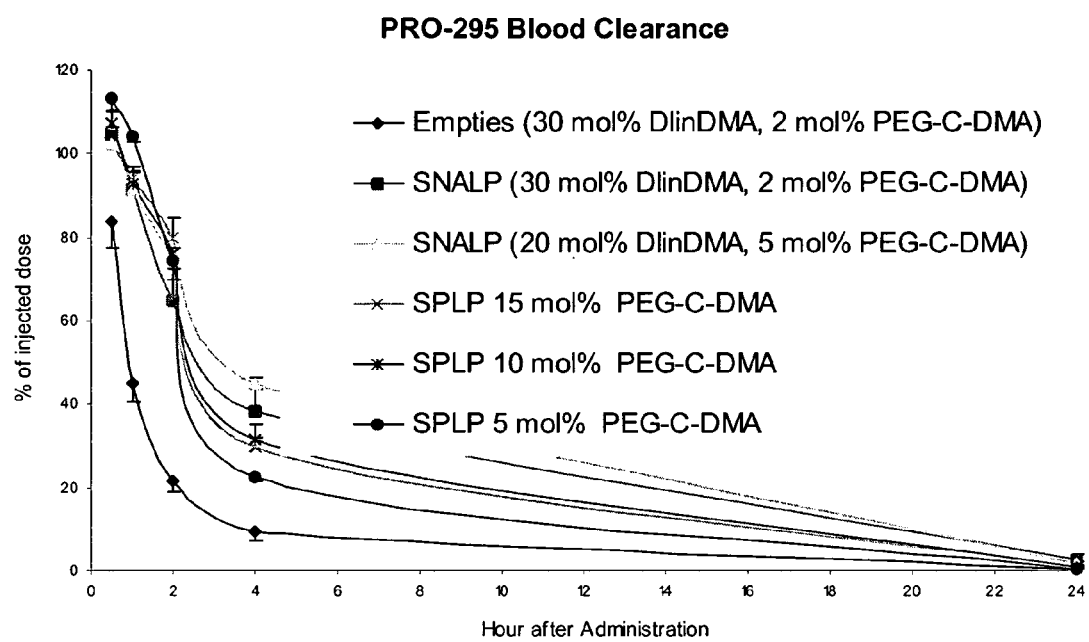
FIG. 10 illustrates data showing the percentage of the injected dose of SPLP, SNALP, or empty vesicles remaining in plasma of male A/J mice following a single intravenous administration of $^3$H—CHE-labeled SPLP or SNALP, or empty vesicles, containing various percentages (i.e., 2%, 5%, 10%, or 15%) of PEG-C-DMA.

The percentage of the injected dose of lipid vesicle remaining in plasma of the mice was determined at 1, 2, 4, and 24 hours following the administration of the $^3$H—CHE-labeled SPLP, SNALP, or empty vesicles. The results are shown in FIG. 10.

Example 12

Biodistribution of Lipid Vesicles Comprising PEG-C-DMA

The example describes experiments conducted to assess the biodistribution of lipid vesicles comprising various percentages of PEG-C-DMA. A single intravenous dose of $^3$H—CHE-labeled SPLP, SNALP, or empty vesicles was administered to Neuro 2A tumor bearing male A/J mice. SPLP comprised the cationic lipid DODMA and SNALP comprised the cationic lipid DLinDMA. The lipid vesicles had the following formulations:

| Group | Treatment | Mol % (DSPC:Chol:PEG-C-DMA:Cationic Lipid) |
|---|---|---|
| A | Empty vesicles | 20:48:2:30 |
| B | SNALP (DlinDMA, PEG-C-DMA) | 20:48:2:30 |
| C | SNALP (DlinDMA, PEG-C-DMA) | 20:55:5:20 |
| D | SPLP (15 mol % PEG-C-DMA) | 20:50:15:15 |
| E | SPLP (10 mol % PEG-C-DMA) | 20:55:10:15 |
| F | SPLP (5 mol % PEG-C-DMA) | 20:60:5:15 |

Figure 11:
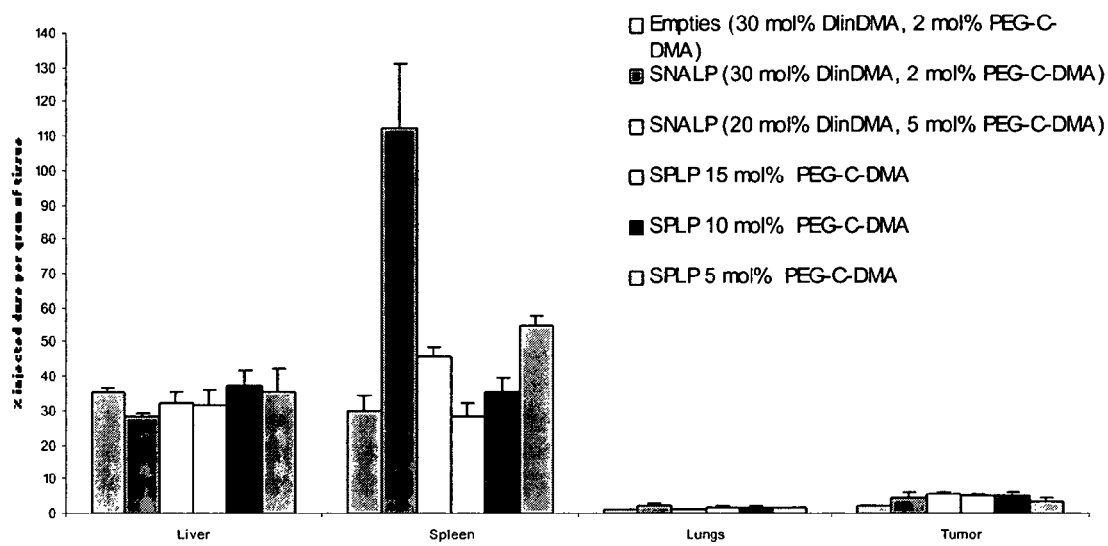
FIG. 11 illustrates data showing the biodistribution SPLP, SNALP or empty vesicles in Neuro-2A tumor-bearing male A/J mice 48 hours after a single intravenous administration of $^3$H—CHE-labelled formulations comprising varying percentages of PEG-C-DMA. The SNALP and empty vesicles comprised DLinDMA. The SPLP comprised DODMA.

The percentage of the injected dose of lipid vesicles was assessed in the liver, spleen, lungs, and tumor of the mice 48 hours after administration of the $^3$H—CHE-labeled vesicles. The results are shown in FIG. 11.

Example 13

Silencing of Gene Expression at a Distal Tumor

This example describes experiments demonstrating gene silencing in distal tumors following administration of SNALP comprising DLinDMA and encapsulating an anti-luciferase siRNA sequence.

Neuro 2A cells were stably transfected with a plasmid encoding luciferase under the control of the CMV promoter (pLO55) to generate Neuro 2A-G cells. Male A/J mice were seeded with the Neuro 2A-G cells. The SNALP encapsulating the anti-luciferase siRNA sequence (i.e., siRNA comprising the following sequence: GAUUAUGUCCGGUUAU-GUAUU (SEQ ID NO:1) and targeting the DNA sequence complementary to: GATTATGTCCGGTTATGTATT (SEQ ID NO:3)) were administered to the Neuro2A-G tumor bearing A/J mice intravenously. The SNALP formulations were as follows:

| Group | Treatment | Mol % (DSPC:Chol: PEG-C-DMA:DLinDMA) |
|---|---|---|
|  | PBS |  |
| A | Anti Luciferase SNALP | 20:48:2:30 |
| B | Control (Invert Sequence) SNALP | 20:48:2:30 |
| C | Anti Luciferase SNALP | 20:55:5:20 |
| D | Control (Invert Sequence) SNALP | 20:55:5:20 |
| E | Anti Luciferase SNALP | 20:55:10:15 |
| F | Control (Invert Sequence) SNALP | 20:55:10:15 |

Figure 12:
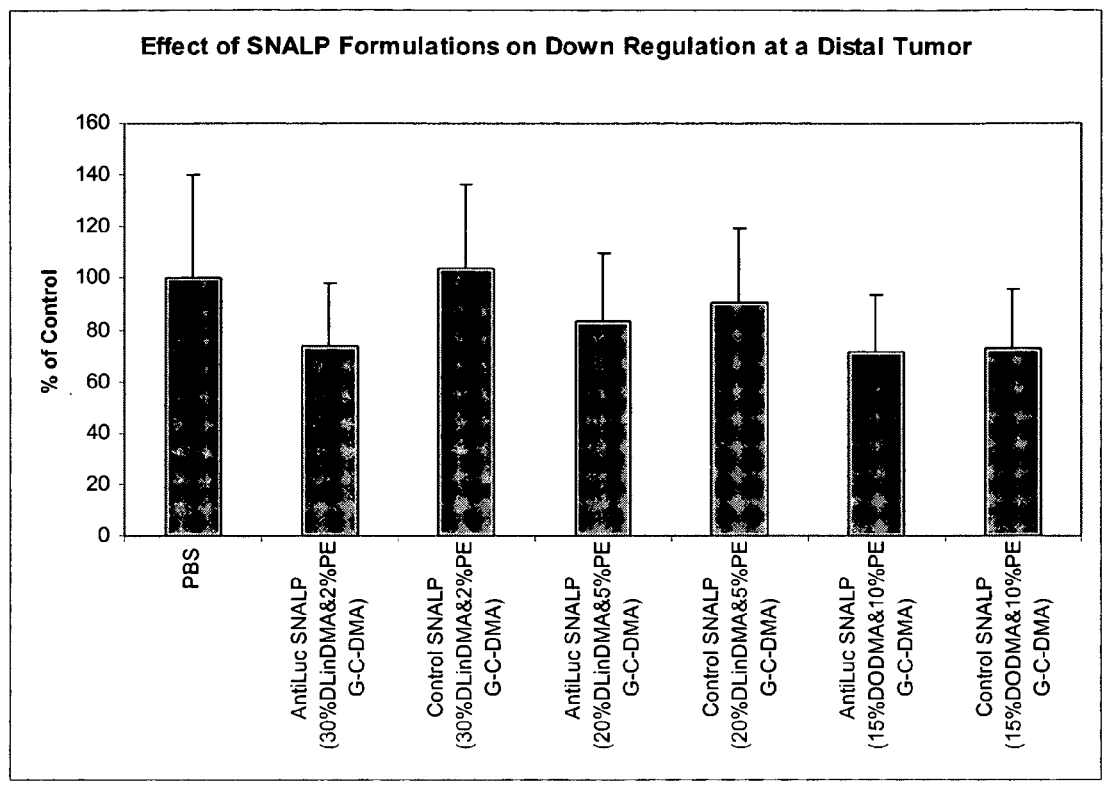
FIG. 12 illustrates data showing silencing of luciferase expression in distal, stable Neuro2A-G tumors in A/J mice 48 hours after intravenous administration of SNALP comprising DLinDMA.

Luciferase gene expression was measured 48 hours following administration of SNALP comprising DLinDMA and encapsulating an anti-luciferase siRNA sequence. The results are shown in FIG. 12.

Example 14

Silencing of Gene Expression in Neuro2A-G Tumor Cells in Vitro

This example describes experiments demonstrating gene silencing in mammalian cells following contact with SNALP comprising DLinDMA and encapsulating an anti-luciferase siRNA sequence described in Example 3 above. Neuro 2A cells were stably transfected with a plasmid encoding luciferase as described in Example 3 above to generate Neuro 2A-G cells. The Neuro 2A-G cell were contacted with SNALP formulations for 24 or 48 hours. The SNALP formulations comprised either PEG-C-DLA ($C_{12}$) or PEG-C-DMA ($C_{14}$) and are as follows:

| Group | Treatment | Mol % (DSPC: Chol:PEG-C-DAA:DLinDMA) |
|---|---|---|
| A | SNALP (PEG-C-DLA) | 20:48:2:30 |
| B | SNALP (PEG-C-DLA) | 20:45:5:30 |
| C | SNALP (PEG-C-DLA) | 20:40:10:30 |
| D | SNALP (PEG-C-DMA) | 20:48:2:30 |

Figure 13:
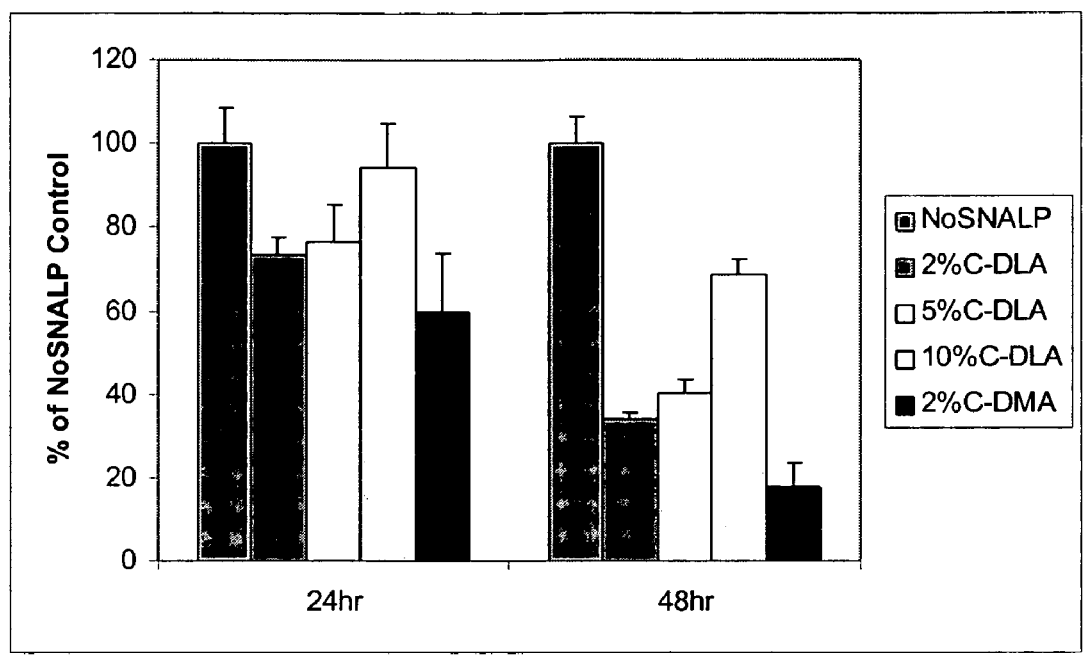
FIG. 13 illustrates data showing silencing of luciferase expression in Neuro2A-G cells following delivery of SNALP formulations comprising DLinDMA and encapsulating anti-luciferase siRNA.

Luciferase gene expression was measured 24 or 48 hours following contacting the Neuro 2A-G cells with SNALP encapsulating an anti-luciferase siRNA sequence. The results are shown in FIG. 13.

Example 15

Silencing of Gene Expression in Neuro2A-G Tumor Cells in Vitro

This example describes experiments demonstrating gene silencing in mammalian cells following contact with SNALP comprising DLinDMA and encapsulating an anti-luciferase siRNA sequence described in Example 3 above. Neuro 2A cells were stably transfected with a plasmid encoding luciferase as described in Example 3 above to generate Neuro 2A-G cells. The Neuro 2A-G cells were contacted with SNALP formulations for 48 hours in the presence and absence of chloroquine. The SNALP formulations contained varying percentages of PEG-C-DMA ($C_{14}$) and either DODMA or DLinDMA. The formulation were as follows:

| Group | Treatment | Mol % (DSPC:Chol:PEG-C-DAA:DLinDMA) |
|---|---|---|
| A | PBS | — |
| B | Naked siRNA | — |
| C | SNALP (PEG-C-DMA) | 20:40:10:30 |
| D | SNALP (PEG-C-DMA) | 20:46:4:30 |
| E | SNALP (PEG-C-DMA) | 20:48:2:30 |
| F | SNALP (PEG-C-DMA) | 20:49:1:30 |

Figure 14:
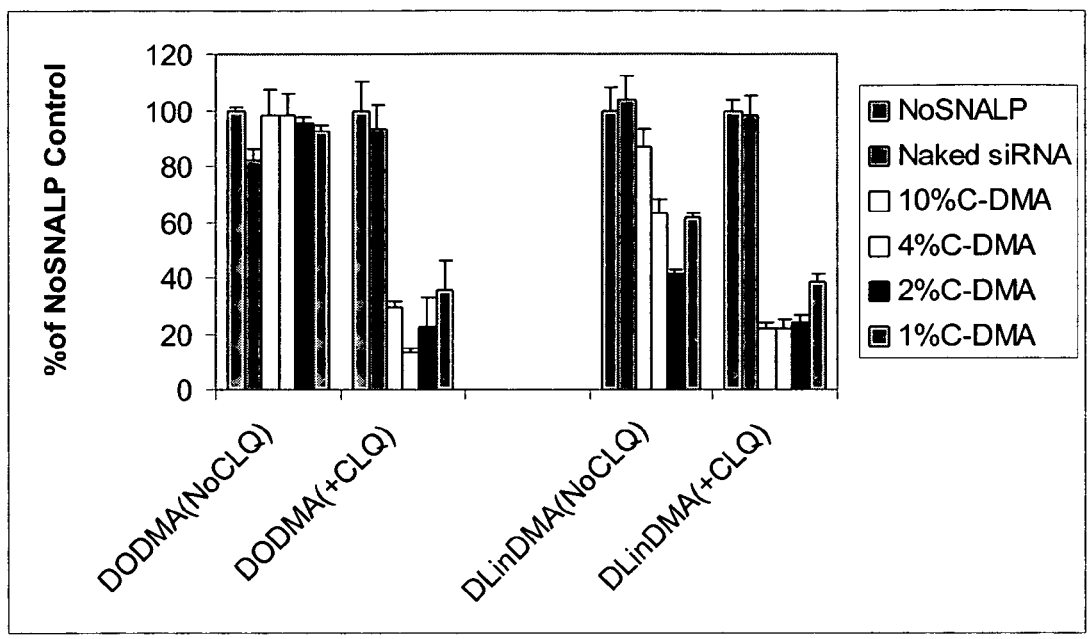
FIG. 14 illustrates data showing silencing of luciferase expression in Neuro2A-G cells following delivery of SNALP formulations comprising DLinDMA and encapsulating anti-luciferase siRNA. Delivery of the SNALP formulations was performed in the absence or presence of chloroquine.

Luciferase gene expression was measured 48 hours following contacting the Neuro 2A-G cells with the SNALP encapsulating an anti-luciferase siRNA sequence. The results are shown in FIG. 14.

Example 16

SNALP Uptake is not Rate Limiting for Gene-Silencing Efficiency

The extent to which formulations are taken up by cells was measured with SNALP incorporating $^3$H-labeled CHE [Bally et al., in *Liposome Technology, Vol. III, pp.* 27-41, CRC Press (1993)]. Neuro2A cells were treated with SNALP containing 3H-labeled CHE for 24 hours. The cells were washed to remove unincorporated SNALP prior to determination of $^3$H—CHE. Uptake is expressed as a percentage of the total activity applied to the cells. Cellular uptake is shown to increase with increasing cationic lipid saturation. Error bars represent standard deviation, n=3. The results are shown in FIG. 15.

Figure 15:
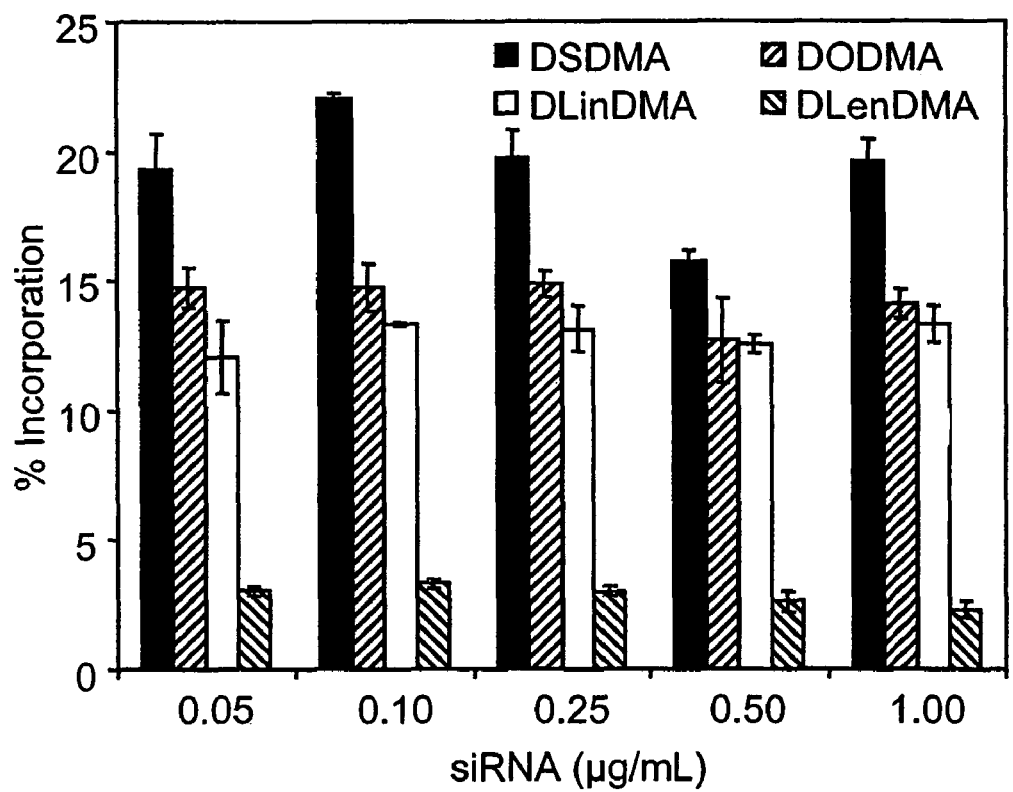
FIG. 15 illustrates data showing cellular uptake of SNALP.

After exposing cells to SNALP formulations for 24 hours, cells were rinsed, lysed and $^3$H—CHE uptake determined (FIG. 15). Uptake of each individual formulation was independent of SNALP concentration, with DSDMA particles exhibiting the greatest degree of uptake. SNALP uptake was observed to decrease with decreasing saturation the DLenDMA formulation appearing particularly limited in this respect. These results are contrary to our expectations, based on the gene silencing results, where the DSDMA formulation is found to be least effective. They suggest that cellular uptake does not limit the gene silencing ability of SNALP, but that endosomal escape, mediated by a fusion event with the endosomal membrane plays an important role in SNALP mediated nucleic acid delivery. Analysis by t-test found all results to be significant ($P<0.05$), apart from the difference between DODMA and DLinDMA at concentrations of 0.10, 0.50 and 1.00 μg/mL.

The uptake process was examined further with the use of fluorescently labelled SNALP. Neuro2A-G cells were treated with formulations containing Cy3-labeled siRNA for 4 hours. After washing and fixing, cell nuclei were stained (blue) with the fluorescent marker DAPI, to more accurately determine the location of the fluorescently labelled siRNA (FIG. 6). In keeping with the results of the $^3$H—CHE uptake experiment, it can be seen that the DSDMA formulation is clearly the most efficient at delivering siRNA to cells. The Cy3 fluorescence (red) is most intense in cells treated with DSDMA containing SNALP. Again, in agreement with the radiolabelled uptake study, as the degree of saturation of the cationic lipid increases, cellular uptake of Cy3 labelled siRNA increases. Again, Cy3 fluorescence is extremely faint for the DLenDMA formulation, indicating poor uptake. Negative controls treated with either naked Cy3-labeled siRNA or unlabeled SNALP revealing no cell associated Cy3 fluorescence.

SNALP labeled with the fluorophore Cy3 were applied to cells and incubated for 4 hours. After washing and fixing, fluorescence microscopy indicates that siRNA uptake, as measured by Cy3 fluorescence, correlates with cationic lipid saturation. Cell nuclei were stained with the fluorophore DAPI. Unlabeled SNALP and naked Cy3-siRNA were used as negative controls Investigating the efficiency of SNALP uptake by incorporation of radiolabelled markers yields further interesting observations (FIG. 5). It might be expected that SNALP uptake would be related to the $pK_a$ of the cationic lipid component; the more positively charged particles having a greater affinity for the negatively charged cell surface and subsequently greater uptake. This hypothesis is borne out by the results of this study. The DSDMA containing formulation, possessing the highest $pK_a$ (~7.6) is clearly taken up most readily, followed by the DODMA and DLinDMA formulations. Curiously, the uptake of the DLenDMA formulation is limited when compared to that of the DLinDMA formulation given that the $pK_a$ of these particles are identical. This suggests that another attribute of these lipids, other than pKa, effects cellular uptake. This finding is unlikely to be a related to differences in particle stability, since time-course studies confirm that the rate of DLenDMA formulation uptake is constant over the 24 h period, suggesting that the formulation remains intact in tissue culture media.

These results suggest that endocytosis is not rate-limiting in gene-silencing in vitro when using encapsulated siRNA. In fact, differences in cellular uptake appear to have remarkably little impact on formulation potency. DLinDMA and DLenDMA formulations, while similar in their ability to inhibit gene expression, are very different in the extent to which they are taken up by cells. Conversely, the DSDMA formulation has almost no capacity for effecting RNA interference, yet it is clearly quite readily taken up by cells. The data suggest that the events which have the greatest effect on the efficiency of gene-silencing occur once the siRNA has been internalized by the cell.

In summary, we have synthesized a homologous series of cationic lipids with incremental degrees of saturation. We show that the degree of saturation of cationic lipids affects lipid pKa, fusogenicity, cellular uptake and gene silencing ability when used to encapsulate and deliver siRNA. Remarkably, more fusogenic cationic lipids are more potent mediators of RNAi, in spite of their reduced efficiency at mediating internalization by the cell. This highlights the relative importance of endosomal release of nucleic acid payloads. This knowledge can be used to enhance the efficacy of other lipidic nucleic acid delivery systems and should be considered in the design of delivery systems for small molecule drugs.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents and PCT publications, and Genbank Accession Nos., are incorporated herein by reference for all purposes.

What is claimed is:

1. A compound having the following structure:

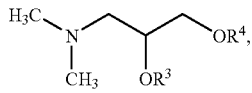

wherein $R^3$ and $R^4$ are both linoleyl.

2. A compound of Formula I having the following structure:

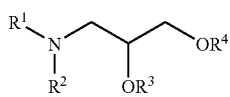

(I)

wherein:

$R^1$ and $R^2$ are independently selected from the group consisting of: H and $C_1$-$C_3$ alkyl; and $R^3$ and $R^4$ are independently selected from the group consisting of alkyl groups having from about 10 to about 20 carbon atoms, wherein both $R^3$ and $R^4$ comprise at least three sites of unsaturation.

3. The compound in accordance with claim 2, wherein $R^3$ and $R^4$ are independently selected from the group consisting of: dodecatrienyl, tetradectrienyl, hexadecatrienyl, linolenyl, and icosatrienyl.

4. The compound in accordance with claim 3, wherein $R^1$ and $R^2$ are methyl; and $R^3$ and $R^4$ are both linolenyl.

* * * * *